(12) United States Patent
Mizuki et al.

(10) Patent No.: US 8,518,560 B2
(45) Date of Patent: Aug. 27, 2013

(54) AROMATIC AMINE DERIVATIVE AND ORGANIC ELECTROLUMINESCENT DEVICE USING THE SAME

(75) Inventors: Yumiko Mizuki, Chiba (JP); Masakazu Funahashi, Chiba (JP); Mitsunori Ito, Chiba (JP); Masahiro Kawamura, Chiba (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 355 days.

(21) Appl. No.: 12/810,317

(22) PCT Filed: Dec. 22, 2008

(86) PCT No.: PCT/JP2008/073337
§ 371 (c)(1),
(2), (4) Date: Aug. 12, 2010

(87) PCT Pub. No.: WO2009/085412
PCT Pub. Date: Jul. 9, 2009

(65) Prior Publication Data
US 2010/0314615 A1   Dec. 16, 2010

(30) Foreign Application Priority Data

Dec. 28, 2007   (JP) ................................. 2007-340948

(51) Int. Cl.
| H01L 51/54 | (2006.01) |
|---|---|
| C07D 407/12 | (2006.01) |
| C07D 407/14 | (2006.01) |
| C07D 405/14 | (2006.01) |
| C07D 409/12 | (2006.01) |
| C07D 421/12 | (2006.01) |
| C07F 7/10 | (2006.01) |

(52) U.S. Cl.
USPC ........... 428/690; 428/917; 313/504; 313/506; 549/460; 549/214; 549/467; 549/43; 549/58; 546/256; 544/356

(58) Field of Classification Search
None
See application file for complete search history.

(56) References Cited

U.S. PATENT DOCUMENTS

| 5,536,949 A | 7/1996 | Hosokawa et al. |
|---|---|---|
| 6,329,084 B1 * | 12/2001 | Tamano et al. ................ 428/690 |
| 6,517,957 B1 | 2/2003 | Senoo et al. |
| 7,504,163 B2 * | 3/2009 | Jarikov ........................ 428/690 |
| 2002/0048688 A1 | 4/2002 | Fukuoka et al. |
| 2004/0081853 A1 | 4/2004 | Conley |
| 2004/0142209 A1 | 7/2004 | Toguchi et al. |
| 2006/0210830 A1 | 9/2006 | Funahashi et al. |
| 2007/0114917 A1 | 5/2007 | Funahashi et al. |
| 2007/0278938 A1 | 12/2007 | Yabunouchi et al. |
| 2008/0004445 A1 | 1/2008 | Hosokawa et al. |
| 2009/0128010 A1 | 5/2009 | Hyun et al. |
| 2011/0156016 A1 * | 6/2011 | Kawamura et al. .............. 257/40 |
| 2012/0112169 A1 * | 5/2012 | Mizuki et al. .................... 257/40 |
| 2012/0153815 A1 | 6/2012 | Hosokawa et al. |

FOREIGN PATENT DOCUMENTS

| JP | 08 012600 | | 1/1996 |
|---|---|---|---|
| JP | 8-199162 A | | 8/1996 |
| JP | 11 003782 | | 1/1999 |
| JP | 11 035532 | | 2/1999 |
| JP | 11-144869 A | | 5/1999 |
| JP | 11-273860 A | | 10/1999 |
| JP | 2001 284050 | | 10/2001 |
| JP | 2002-116563 | * | 4/2002 |
| JP | 3508984 | | 1/2004 |
| JP | 2006 256979 | | 9/2006 |
| WO | 94 06157 | | 3/1994 |
| WO | WO 00/39247 A1 | | 7/2000 |
| WO | WO 2004/040669 A1 | | 5/2004 |
| WO | WO 2007/021117 A1 | | 2/2007 |
| WO | 2007 058035 | | 5/2007 |
| WO | 2007 123137 | | 11/2007 |
| WO | 2007 125714 | | 11/2007 |

OTHER PUBLICATIONS

Office Action issued Jul. 24, 2012 in Japanese Patent Application No. 2009-548030.

* cited by examiner

Primary Examiner — Dawn Garrett

(74) Attorney, Agent, or Firm — Oblon, Spivak, McClelland, Maier & Neustadt, L.L.P.

(57) ABSTRACT

Provided are: an aromatic amine derivative in which a terminal substituent such as a dibenzofuran ring or a dibenzothiophene ring is bonded to a nitrogen atom directly or through an arylene group or the like; an organic electroluminescence device including an organic thin film layer formed of one or more layers including a light emitting layer and interposed between a cathode and an anode in which a layer of the organic thin film layer contains the aromatic amine derivative by itself or as a component of a mixture, and the device has a long lifetime and high luminous efficiency; and an aromatic amine derivative for realizing the device.

21 Claims, No Drawings

AROMATIC AMINE DERIVATIVE AND ORGANIC ELECTROLUMINESCENT DEVICE USING THE SAME

TECHNICAL FIELD

The present invention relates to an aromatic amine derivative and an organic electroluminescence device using the same, in particular, an organic electroluminescence device having a long lifetime and high luminous efficiency, and an aromatic amine derivative for realizing the device.

BACKGROUND ART

A large number of organic electroluminescence (EL) devices each using an organic substance have been developed because of their potential to find applications in solid light emission type, inexpensive, large-area, full-color display devices. In general, an organic EL device is constituted of a light emitting layer and a pair of opposing electrodes between which the layer is interposed. Light emission is the phenomenon in which when an electric field is applied between bath the electrodes, an electron is injected from a cathode side and a hole is injected from an anode side, and further, the electron recombines with the hole in the light emitting layer to produce an excited state, and energy generated upon return of the excited state to a ground state is emitted as light.

A conventional organic EL device was driven at a voltage higher than the voltage at which an inorganic light emitting diode is driven, and had emission luminance and luminous efficiency lower than those of the diode. In addition, the properties of the device deteriorated remarkably, so the device has not been put into practical use. A recent organic EL device has been gradually improved, but actually, additionally high luminous efficiency and an additionally long lifetime of the device are still requested.

For example, a technology involving the use of a single monoanthracene compound as an organic light emitting material has been disclosed (Patent Document 1). However, the technology is not practical because of, for example, the following reasons. That is, a luminance of only 1650 cd/m$^2$ is obtained at a current density of 165 mA/cm$^2$, and efficiency is 1 cd/A, which is an extremely low value. In addition, a technology involving the use of a single bisanthracene compound as an organic light emitting material has been disclosed (Patent Document 2). However, an improvement for putting the technology into practical use has been requested because efficiency is as low as about 1 to 3 cd/A. Meanwhile, a long-lifetime organic EL device using a distyryl compound as an organic light emitting material and styrylamine or the like added to the compound has been proposed (Patent Document 3) However, an additional improvement of the device has been requested because the device does not have a sufficient lifetime.

In addition, a technology involving the use of a monoanthracene or bisanthracene compound and a distyryl compound in an organic light emitting medium layer has been disclosed (Patent Document 4). In such technology, however, an emission spectrum shifts to longer wavelengths owing to the conjugate structure of the styryl compound, and hence a color purity deteriorates.

In addition, Patent Document 5 discloses an invention in which an aromatic amine derivative having an arylene group at its center and a dibenzofuran ring bonded to a nitrogen atom is used as a hole transporting material, and Patent Document 6 discloses an invention in which an aromatic amine derivative having a dibenzofuran ring, dibenzothiophene ring, benzofuran ring, benzothiophene ring, or the like bonded to a nitrogen atom through an arylene group is used as a hole transporting material. However, there are no cases where the derivatives are used as light emitting materials.

Patent Document 1: JP 11-3782 A
Patent Document 2: JP 08-12600 A
Patent Document 3: WO 94/006157 A1
Patent Document 4: JP 2001-284050 A
Patent Document 5: JP 3508984 B2
Patent Document 6: WO 07/125714 A1

DISCLOSURE OF THE INVENTION

Problems to be Solved by the Invention

The present invention has been made to solve the above-mentioned problems, and an object of the present invention is to provide an organic EL device having a long lifetime and high luminous efficiency, and an aromatic amine derivative for realizing the device.

Means for Solving the Problems

The inventors of the present invention have made extensive studies with a view to developing an aromatic amine derivative having the preferred properties and an organic EL device using the derivative. As a result, the inventors have achieved high luminous efficiency and a lengthened lifetime by finding the following fact. That is, when an aromatic amine derivative having a fused aromatic hydrocarbon group on its central skeleton where a rigid, sterically bulky terminal substituent such as a dibenzofuran ring or a dibenzothiophene ring is bonded to a nitrogen atom directly or through an arylene group or the like is used particularly as a light emitting material, concentration quenching hardly occurs through an influence of the terminal substituent. The present invention has been completed on the basis of such finding.

That is, the present invention provides an aromatic amine derivative represented by the following general formula (1):

Aromatic amine derivative represented by the following general formula (1):

where $Ar_0$ represents a substituted or unsubstituted, divalent fused aromatic hydrocarbon group having 10 to 50 ring-forming carbon atoms, and $Ar_1$ to $Ar_4$ each independently represent a substituted or unsubstituted aryl group having 6 to 50 ring-forming carbon atoms, a substituted or unsubstituted alkyl group having 1 to 50 carbon atoms, a substituted or unsubstituted cycloalkyl group having 3 to 50 ring-forming carbon atoms, a substituted or unsubstituted aralkyl group having 7 to 50 ring-forming carbon atoms, or a substituted or unsubstituted heterocyclic group having 5 to 50 ring-forming atoms, provided that one or more of $Ar_1$ to $Ar_4$ each represent a group represented by the following general formula (2) or (3):

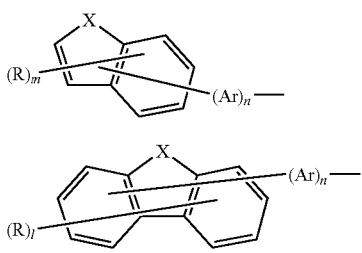

where n represents an integer of 0 to 3, m represents an integer of 0 to 5, l represents an integer of 0 to 7, X represents oxygen (O), sulfur (S), or selenium (Se), Ar represents a substituted or unsubstituted arylene group having 6 to 60 ring-forming carbon atoms, R represents a substituted or unsubstituted aryl group having 6 to 60 ring-forming carbon atoms, a substituted or unsubstituted alkyl group having 1 to 50 carbon atoms, an amino group, a substituted or unsubstituted alkoxy group having 1 to 50 carbon atoms, a substituted or unsubstituted aryloxy group having 7 to 50 ring-forming carbon atoms, a substituted or unsubstituted arylthio group having 6 to 50 ring-forming atoms, a substituted or unsubstituted alkoxycarbonyl group having 1 to 50 carbon atoms, a halogen atom, a cyano group, a nitro group, a hydroxyl group, a silyl group, or a carboxyl group, when n, m, or l represents 2 or more, multiple Ar's or multiple R's may be identical to or different from each other, and when multiple R's are present, the multiple R's may be bonded to each other to form a saturated or unsaturated, five- or six-membered cyclic structure that may be substituted, provided that: when n=0, a five-membered ring portion including X in the general formula (2) is free from being directly bonded to N bonded to $Ar_0$; and in the general formula (3), a case where $(R)_l$ and $(Ar)_n$ are bonded to a five-membered ring portion including X is excluded.

In addition, the present invention provides an organic EL device including an organic thin film layer formed of one or more layers including at least a light emitting layer and interposed between a cathode and an anode, in which at least one layer of the organic thin film layer contains the aromatic amine derivative by itself or as a component of a mixture.

Effects of the Invention

The organic EL device using the aromatic amine derivative of the present invention has high luminous efficiency, hardly deteriorates even when used for a long time period, and has a long lifetime.

BEST MODE FOR CARRYING OUT THE INVENTION

An aromatic amine derivative of the present invention is a compound represented by the following general formula (1).

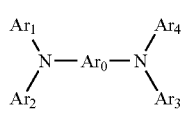

(1)

In the general formula (1), $Ar_0$ represents a substituted or unsubstituted, divalent fused aromatic hydrocarbon group having 10 to 50 ring-forming carbon atoms.

Examples of the fused aromatic hydrocarbon group represented by $Ar_0$ include a naphthylene group, an anthracenylene group, a phenanthrylene group, a chrysenylene group, a pyrenylene group, a benzoanthracenylene group, a fluoranthenylene group, a benzofluoranthenylene group, a perylenylene group, a coronenylene group, a picenylene group, a diphenylanthracenylene group, a fluorenylene group, a triphenylylene group, a rubicenylene group, a phenylanthracenylene group, a bisanthracenylene group, a dianthracenylbenzynylene group, and a dibenzoanthracenylene group. Of those, a naphthylene group, an anthracenylene group, a phenanthrylene group, a chrysenylene group, a pyrenylene group, and a benzoanthracenylene group are preferred.

In addition, it is preferred that —$NAr_1Ar_2$ and —$NAr_3Ar_4$ be bonded to 2- and 6-positions of the naphthylene group, respectively, —$NAr_1Ar_2$ and —$NAr_3Ar_4$ be bonded to 1- and 4-positions of the naphthylene group, respectively, —$NAr_1Ar_2$ and —$NAr_3Ar_4$ be bonded to 9- and 10-positions of the anthracenylene group, respectively, —$NAr_1Ar_2$ and —$NAr_3Ar_4$ be bonded to 2- and 6-positions of the anthracenylene group, respectively, —$NAr_1Ar_2$ and —$NAr_3Ar_4$ be bonded to 2- and 7-positions of the phenanthrylene group, respectively, —$NAr_1Ar_2$ and —$NAr_3Ar_4$ be bonded to 6- and 12-positions of the chrysenylene group, respectively, —$NAr_1Ar_2$ and —$NAr_3Ar_4$ be bonded to 1- and 6-positions of the pyrenylene group, respectively, —$NAr_1Ar_2$ and —$NAr_3Ar_4$ be bonded to 2- and 7-positions of the pyrenylene group, respectively, —$NAr_1Ar_2$ and —$NAr_3Ar_4$ be bonded to 7- and 12-positions of the benzoanthracenylene group, respectively, or —$NAr_1Ar_2$ and —$NAr_3Ar_4$ be bonded to 7- and 12-positions of the benzofluoranthenylene group, respectively.

In the general formula (1), $Ar_1$ to $Ar_4$ each independently represent a substituted or unsubstituted aryl group having 6 to 50 ring-forming carbon atoms (or preferably 6 to 20 ring-forming carbon atoms), a substituted or unsubstituted alkyl group having 1 to 50 carbon atoms (or preferably 1 to 20 carbon atoms), a substituted or unsubstituted cycloalkyl group having 3 to 50 ring-forming carbon atoms (or preferably 5 to 12 ring-forming carbon atoms), a substituted or unsubstituted aralkyl group having 7 to 50 ring-forming carbon atoms (or preferably 7 to 20 ring-forming carbon atoms), or a substituted or unsubstituted heterocyclic group having 5 to 50 ring-forming atoms (or preferably 5 to 20 ring-forming atoms).

Examples of the aryl group represented by any one of $Ar_1$ to $Ar_4$ include a phenyl group, a 2-methylphenyl group, a 3-methylphenyl group, a 4-methylphenyl group, a 4-ethylphenyl group, a biphenyl group, a 4-methylbiphenyl group, a 4-ethylbiphenyl group, a 4-cyclohexylbiphenyl group, a terphenyl group, a 3,5-dichlorophenyl group, a naphthyl group, a 5-methylnaphthyl group, an anthryl group, a pyrenyl group, a chrysenyl group, a fluoranthenyl group, and a perylenyl group.

Examples of the alkyl group represented by any one of $Ar_1$ to $Ar_4$ include a methyl group, an ethyl group, a propyl group, an isopropyl group, a butyl group, a sec-butyl group, a tert-butyl group, a pentyl group, a hexyl group, a heptyl group, an octyl group, a stearyl group, a 2-phenylisopropyl group, a trichloromethyl group, a trifluoromethyl group, a benzyl group, an α-phenoxybenzyl group, an α,α-dimethylbenzyl group, an α,α-methylphenylbenzyl group, an α,α-ditrifluoromethylbenzyl group, a triphenylmethyl group, and an α-benzyloxybenzyl group.

Examples of the cycloalkyl group represented by any one of $Ar_1$ to $Ar_4$ include a cyclopropyl group, a cyclobutyl group, a cyclopentyl group, a cyclohexyl group, a cycloheptyl group, a cyclooctyl group, a cyclononyl group, a bicycloheptyl group, a bicyclooctyl group, a tricycloheptyl group, and an adamantyl group. Of those, a cyclopentyl group, a cyclohexyl group, a cycloheptyl group, a bicycloheptyl group, a bicyclooctyl group, and an adamantyl group are preferred.

Examples of the aralkyl group represented by any one of $Ar_1$ to $Ar_4$ include a benzyl group, a 1-phenylethyl group, a 2-phenylethyl group, a 1-phenylisopropyl group, a 2-phenylisopropyl group, a phenyl-t-butyl group, an α-naphthylmethyl group, a 1-α-naphthylethyl group, a 2-α-naphthylethyl group, a 1-α-naphthylisopropyl group, a 2-α-naphthylisopropyl group, a β-naphthylmethyl group, a 1-β-naphthylethyl group, a 2-β-naphthylethyl group, a 1-β-naphthylisopropyl group, a 2-β-naphthylisopropyl group, a 1-pyrrolylmethyl group, a 2-(1-pyrrolyl)ethyl group, a p-methylbenzyl group, an m-methylbenzyl group, an o-methylbenzyl group, a p-chlorobenzyl group, an m-chlorobenzyl group, an o-chlorobenzyl group, a p-bromobenzyl group, an m-bromobenzyl group, an o-bromobenzyl group, a p-iodobenzyl group, an m-iodobenzyl group, an o-iodobenzyl group, a p-hydroxybenzyl group, an m-hydroxybenzyl group, an o-hydroxybenzyl group, a p-aminobenzyl group, an m-aminobenzyl group, an o-aminobenzyl group, a p-nitrobenzyl group, an m-nitrobenzyl group, an o-nitrobenzyl group, a p-cyanobenzyl group, an m-cyanobenzyl group, an o-cyanobenzyl group, a 1-hydroxy-2-phenylisopropyl group, and a 1-chloro-2-phenylisopropyl group.

Examples of the heterocyclic group represented by any one of $Ar_1$ to $Ar_4$ include residues of imidazole, benzimidazole, pyrrole, furan, thiophene, oxadiazoline, indoline, carbazole, pyridine, quinoline, isoquinoline, benzoquinone, pyralozine, imidazolidine, and piperidine.

It should be noted that one or more of $Ar_1$ to $Ar_4$ in the general formula (1) each represent a group represented by the following general formula (2) or (3).

In the general formula (1), $Ar_1$ and $Ar_3$ each preferably represent a group represented by the general formula (2) or (3), or all of $Ar_1$ to $Ar_4$ each more preferably represent a group represented by the general formula (2) or (3).

In addition, one or more of $Ar_1$ to $Ar_4$ in the general formula (1) each preferably represent a group represented by the general formula (3).

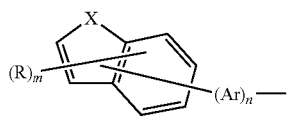

(2)

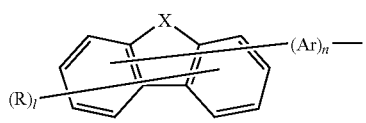

(3)

In the general formulae (2) and (3), n represents an integer of 0 to 3 (or preferably 0), m represents an integer of 0 to 5 (or preferably 0 to 2), and l represents an integer of 0 to 7 (or preferably 0 to 4).

In addition, when n, m, or l represents 2 or more, multiple Ar's or multiple R's may be identical to or different from each other.

It should be noted that, when n=0 in the general formula (2), a five-membered ring portion including X is not directly bonded to N bonded to $Ar_0$. In addition, in the general formula (3), the case where $(R)_1$ and $(Ar)_n$ are bonded to a five-membered ring portion including X is excluded.

In each of the general formulae (2) and (3), X represents oxygen (O), sulfur (S), or selenium (Se), or preferably an oxygen atom or a sulfur atom.

In addition, when n in the general formula (3) represents 0, it is preferred that X represent an oxygen atom or a sulfur atom, and a bonding position be present at a 2- or 4-position (or more preferably the 2-position) of a fused ring including X.

In each of the general formulae (2) and (3), Ar represents a substituted or unsubstituted arylene group having 6 to 60 ring-forming carbon atoms (or preferably 6 to 20 ring-forming carbon atoms), and examples of the arylene group include groups obtained by making the specific examples of the aryl group described for $Ar_1$ to $Ar_4$ divalent.

In each of the general formulae (2) and (3), R represents a substituted or unsubstituted aryl group having 6 to 60 ring-forming carbon atoms (or preferably 6 to 20 ring-forming carbon atoms), a substituted or unsubstituted alkyl group having 1 to 50 carbon atoms (or preferably 1 to 20 carbon atoms), an amino group, a substituted or unsubstituted alkoxy group having 1 to 50 carbon atoms (or preferably 1 to 6 carbon atoms), a substituted or unsubstituted aryloxy group having 6 to 50 ring-forming carbon atoms (or preferably 6 to 18 ring-forming carbon atoms), a substituted or unsubstituted arylthio group having 6 to 50 ring-forming atoms (or preferably 6 to 18 ring-forming carbon atoms), a substituted or unsubstituted alkoxycarbonyl group having 1 to 50 carbon atoms, a halogen atom, a cyano group, a nitro group, a hydroxyl group, a silyl group, or a carboxyl group. In addition, when multiple R's are present, the multiple R's may be bonded to each other to form a saturated or unsaturated, five- or six-membered cyclic structure that may be substituted.

In each of the general formulae (2) and (3), R preferably represents a silyl group.

Specific examples of the aryl group and the alkyl group each represented by R include the same examples as those of the aryl group and the alkyl group described for $Ar_1$ to $Ar_4$.

In addition, examples of the alkoxy group represented by R include a methoxy group, an ethoxy group, a propoxy group, an isopropoxy group, a butoxy group, an isobutoxy group, an sec-butoxy group, a tert-butoxy group, various pentyloxy groups, and various hexyloxy groups.

The alkoxycarbonyl group represented by R is represented as —COOZ, and examples of Z include the same examples as those of the alkyl group described for $Ar_1$ to $Ar_4$.

The aryloxy group and the arylthio group each represented by R are represented as —OY and —SY, respectively, and examples of Y include the same examples as those of the aryl group described for $Ar_1$ to $Ar_4$.

In the general formulae (2) and (3), m and l each preferably represent 0.

It should be noted that the number of carbon atoms or atoms of each group of each of the above-mentioned general formulae is a number excluding that of a substituent. In addition, the number of carbon atoms of an aralkyl group is the number of carbon atoms of an aryl portion.

An arbitrary substituent in the "substituted or unsubstituted . . . group" in each of the above-mentioned general formulae is, for example, a substituted or unsubstituted aryl group having 6 to 50 ring-forming carbon atoms, a substituted or unsubstituted alkyl group having 1 to 50 carbon atoms, a substituted or unsubstituted alkoxy group having 1 to 50 carbon atoms, a substituted or unsubstituted aralkyl group having 7 to 50 ring-forming carbon atoms, a substituted or unsubstituted aryloxy group having 6 to 50 ring-forming carbon atoms, a substituted or unsubstituted arylthio group having 6 to 50 ring-forming carbon atoms, a substituted or unsubstituted alkoxycarbonyl group having 1 to 50 carbon atoms, an amino group, a halogen atom, a cyano group, a nitro group, a hydroxyl group, or a carboxyl group.

Of those, an alkyl group having 1 to 10 carbon atoms, a cycloalkyl group having 5 to 7 carbon atoms, and an alkoxy group having 1 to 10 carbon atoms are preferred, an alkyl group having 1 to 6 carbon atoms and a cycloalkyl group having 5 to 7 carbon atoms are more preferred, and a methyl group, an ethyl group, an n-propyl group, an isopropyl group, an n-butyl group, an sec-butyl group, a tert-butyl group, an n-pentyl group, an n-hexyl group, a cyclopentyl group, and a cyclohexyl group are particularly preferred.

Specific examples of the aromatic amine derivative represented by the general formula (1) of the present invention are shown below. However, the present invention is not limited to these exemplified compounds.

TABLE 1

| No | $Ar_0$ | $Ar_1$ | $Ar_2$ | $Ar_3$ | $Ar_4$ |
|---|---|---|---|---|---|
| D-1 | | | | | |
| D-2 | | | | | |
| D-3 | | | | | |
| D-4 | | | | | |
| D-5 | | | | | |
| D-6 | | | | | |

TABLE 1-continued
| No | Ar₀ | Ar₁ | Ar₂ | Ar₃ | Ar₄ |
|----|-----|-----|-----|-----|-----|
| D-7 | 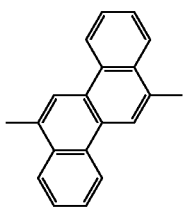 | 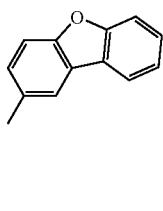 | 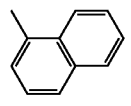 | 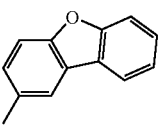 | 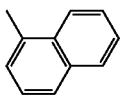 |
| D-8 | 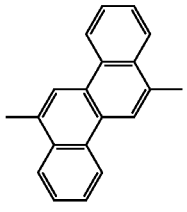 | 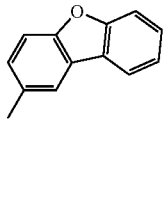 | 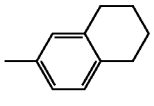 | 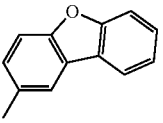 | 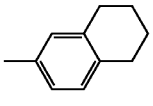 |
| D-9 | 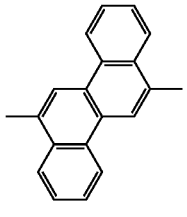 | 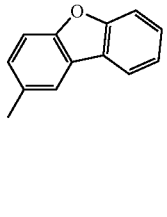 | 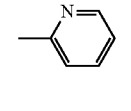 | 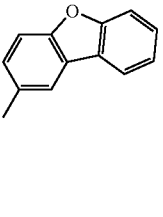 | 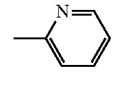 |
| D-10 | 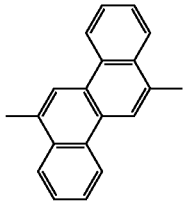 | 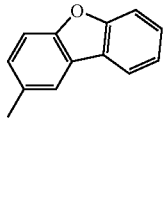 | 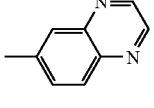 | 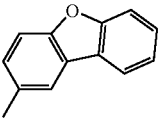 | 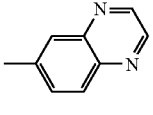 |
TABLE 2
| No | Ar₀ | Ar₁ | Ar₂ | Ar₃ | Ar₄ |
|----|-----|-----|-----|-----|-----|
| D-11 | 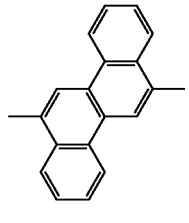 | 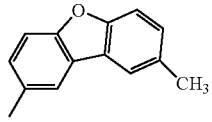 | 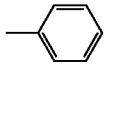 | 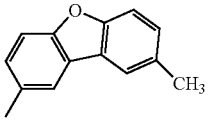 | 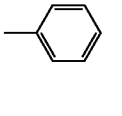 |
| D-12 | 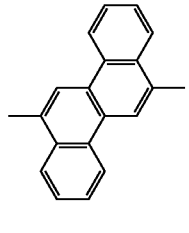 | 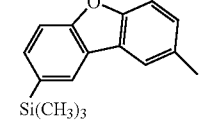 | 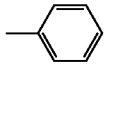 | 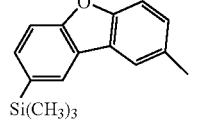 | 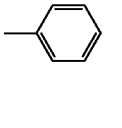 |

TABLE 2-continued

| No | Ar₀ | Ar₁ | Ar₂ | Ar₃ | Ar₄ |
|---|---|---|---|---|---|
| D-13 | | | | | |
| D-14 | | | | | |
| D-15 | | | | | |
| D-16 | | | | | |
| D-17 | | | | | |
| D-18 | | | | | |
| D-19 | | | | | |

TABLE 2-continued
| No | Ar₀ | Ar₁ | Ar₂ | Ar₃ | Ar₄ |
|---|---|---|---|---|---|
| D-20 | 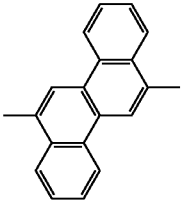 | 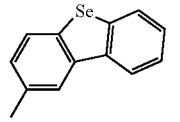 | 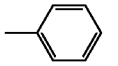 | 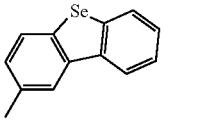 |  |
TABLE 3
| No | Ar₀ | Ar₁ | Ar₂ | Ar₃ | Ar₄ |
|---|---|---|---|---|---|
| D-21 | 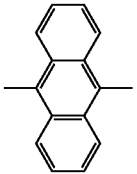 | 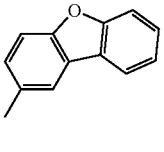 | 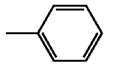 | 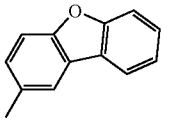 |  |
| D-22 | 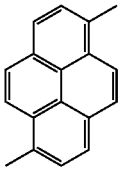 | 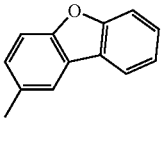 | 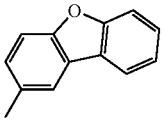 | 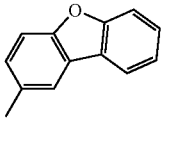 | 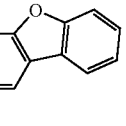 |
| D-23 | 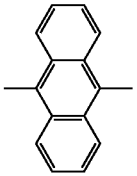 | 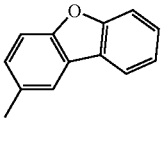 | 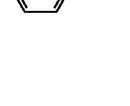 | 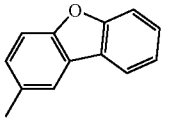 | 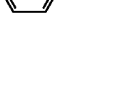 |
| D-24 | 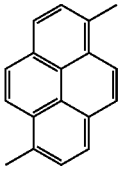 | 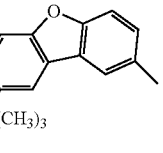 | 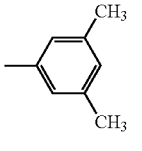 | 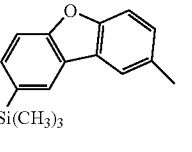 | 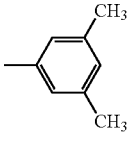 |
| D-25 | 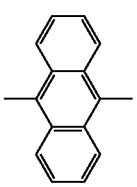 | 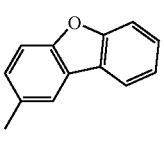 | 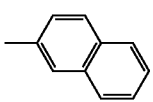 | 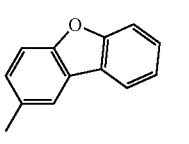 | 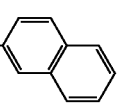 |
| D-26 | 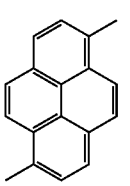 | 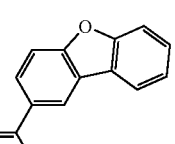 | 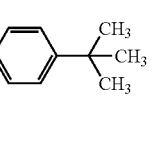 | 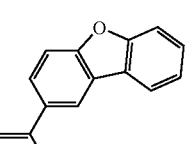 | 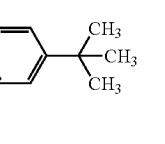 |

US 8,518,560 B2
TABLE 3-continued
| No | Ar₀ | Ar₁ | Ar₂ | Ar₃ | Ar₄ |
|---|---|---|---|---|---|
| D-27 | 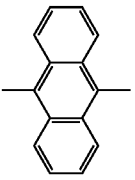 | 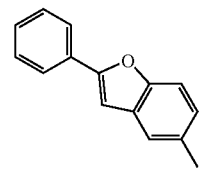 | 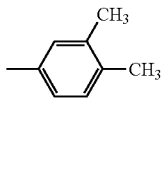 | 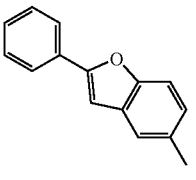 | 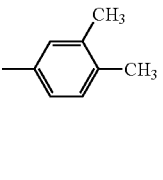 |
| D-28 | 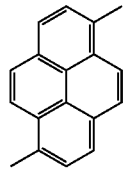 | 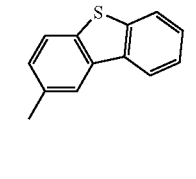 | 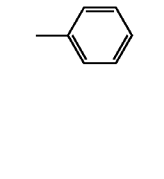 | 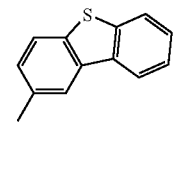 | 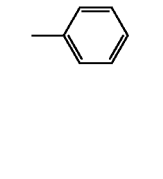 |
| D-29 | 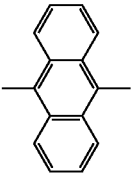 | 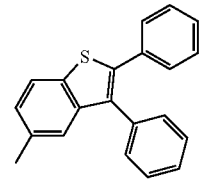 | 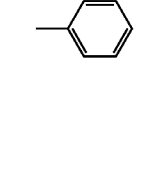 | 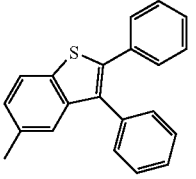 | 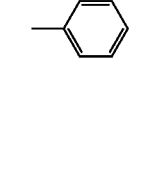 |
| D-30 | 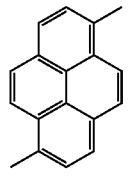 | 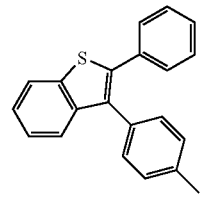 | 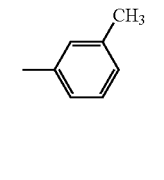 | 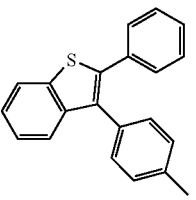 | 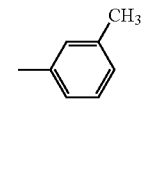 |
TABLE 4
| No | Ar₀ | Ar₁ | Ar₂ | Ar₃ | Ar₄ |
|---|---|---|---|---|---|
| D-31 | 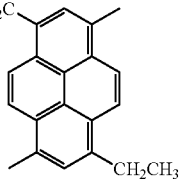 | 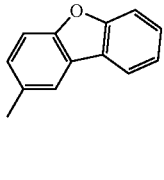 | 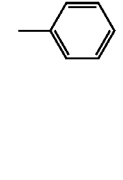 | 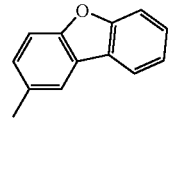 | 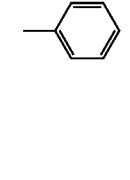 |
| D-32 | 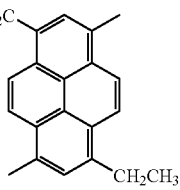 | 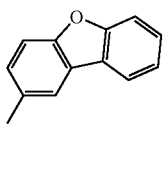 | 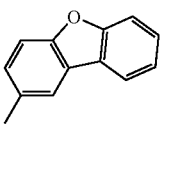 | 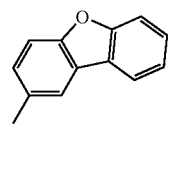 | 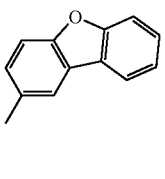 |
| D-33 | 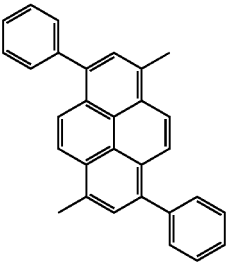 | 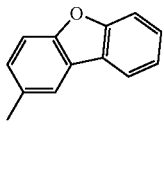 | 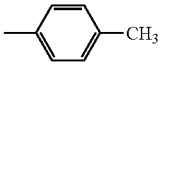 | 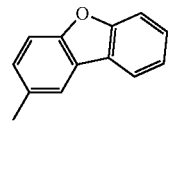 | 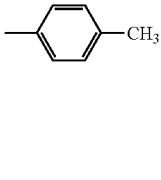 |

TABLE 4-continued

| No | Ar₀ | Ar₁ | Ar₂ | Ar₃ | Ar₄ |
|---|---|---|---|---|---|
| D-34 | 1,3-dimethyl-6,8-diphenylpyrene | dibenzofuran-Si(CH₃)₃ | 2,4-dimethylphenyl | dibenzofuran-methyl | 2,4-dimethylphenyl |
| D-35 | 2,6-dimethyl-9,10-di(2-naphthyl)anthracene | methyldibenzofuran | 2-naphthyl | methyldibenzofuran | 2-naphthyl |
| D-36 | 2,6-dimethyl-9,10-di(2-naphthyl)anthracene | methyldibenzofuran | phenyl | methyldibenzofuran | phenyl |
| D-37 | 9,10-dimethyl-2,6-dicyclohexylanthracene | methyldibenzofuran | methyldibenzofuran | methyldibenzofuran | methyldibenzofuran |
| D-38 | 9,10-dimethyl-2,6-dicyclohexylanthracene | methyldibenzofuran | 4-methylphenyl | methyldibenzofuran | 4-methylphenyl |

TABLE 4-continued

| No | Ar₀ | Ar₁ | Ar₂ | Ar₃ | Ar₄ |
|---|---|---|---|---|---|
| D-39 | 1,5-diisopropyl-3,7-dimethylnaphthalene | 2-methyl-8-trimethylsilyl-dibenzofuran | 3,5-dimethylphenyl | 2-methyl-8-trimethylsilyl-dibenzofuran | 3,5-dimethylphenyl |
| D-40 | 1,5-diisopropyl-3,7-dimethylnaphthalene | 2-methyldibenzofuran | 2-methylnaphthyl | 2-methyldibenzofuran | 2-methylnaphthyl |

TABLE 5

| No | Ar₀ | Ar₁ | Ar₂ | Ar₃ | Ar₄ |
|---|---|---|---|---|---|
| D-41 | 2,7-disubstituted pyrene | 2-methyldibenzofuran | phenyl | 2-methyldibenzofuran | phenyl |
| D-42 | 2,7-disubstituted pyrene | 2-methyldibenzofuran | 2-methyldibenzofuran | 2-methyldibenzofuran | 2-methyldibenzofuran |
| D-43 | 1,6-di(2-naphthyl)-3,8-dimethylpyrene | 2-methyldibenzofuran | 4-methylphenyl | 2-methyldibenzofuran | 4-methylphenyl |
| D-44 | 1,6-di(2-naphthyl)-3,8-dimethylpyrene | 2-methyl-8-trimethylsilyl-dibenzofuran | 3,5-dimethylphenyl | 2-methyl-8-trimethylsilyl-dibenzofuran | 3,5-dimethylphenyl |

TABLE 5-continued

| No | Ar₀ | Ar₁ | Ar₂ | Ar₃ | Ar₄ |
|---|---|---|---|---|---|
| D-45 | [2,6-diphenylanthracene structure] | [methyldibenzofuran] | [methylnaphthalene] | [methyldibenzofuran] | [methylnaphthalene] |
| D-46 | [2,6-diphenylanthracene structure] | [methyldibenzofuran] | [phenyl] | [methyldibenzofuran] | [phenyl] |
| D-47 | [anthracene with biphenyl substituents] | [methyldibenzofuran] | [methyldibenzofuran] | [methyldibenzofuran] | [methyldibenzofuran] |
| D-48 | [anthracene with biphenyl substituents] | [methyldibenzofuran] | [4-methylphenyl] | [methyldibenzofuran] | [4-methylphenyl] |
| D-49 | [di-tert-butylanthracene structure] | [trimethylsilyl-methyldibenzofuran] | [2,4-dimethylphenyl] | [trimethylsilyl-methyldibenzofuran] | [2,4-dimethylphenyl] |

TABLE 5-continued
| No | Ar₀ | Ar₁ | Ar₂ | Ar₃ | Ar₄ |
|----|-----|-----|-----|-----|-----|
| D-50 | 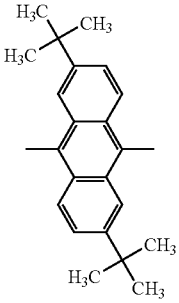 | 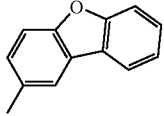 | 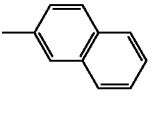 | 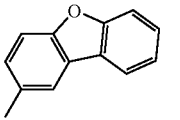 | 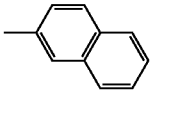 |
TABLE 6
| No | Ar₀ | Ar₁ | Ar₂ | Ar₃ | Ar₄ |
|----|-----|-----|-----|-----|-----|
| D-51 | 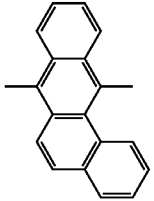 | 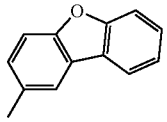 | 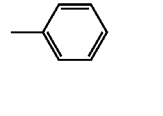 | 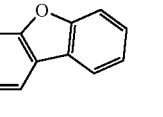 | 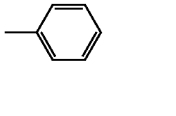 |
| D-52 | 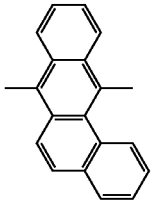 | 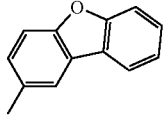 | 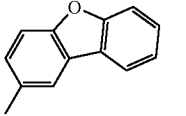 | 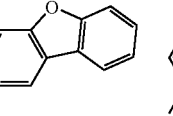 | 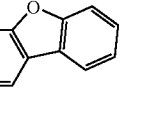 |
| D-53 | 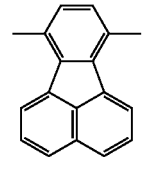 | 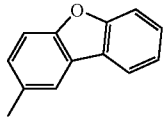 | 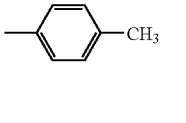 | 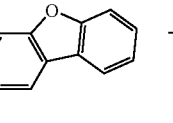 | 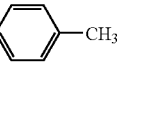 |
| D-54 | 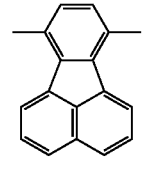 | 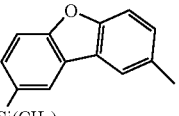 | 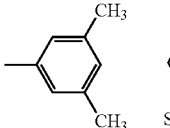 | 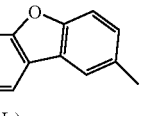 | 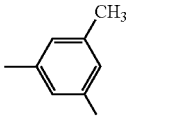 |
| D-55 | 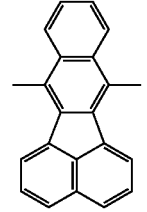 | 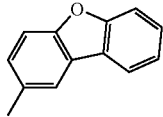 | 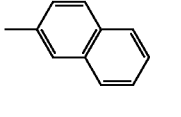 | 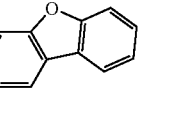 | 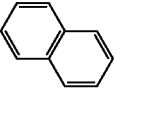 |

TABLE 6-continued
| No | Ar₀ | Ar₁ | Ar₂ | Ar₃ | Ar₄ |
|---|---|---|---|---|---|
| D-56 | 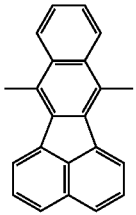 | 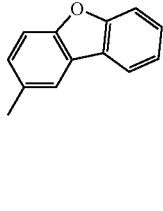 |  | 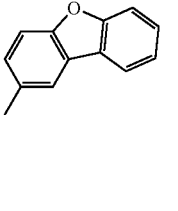 |  |
| D-57 | 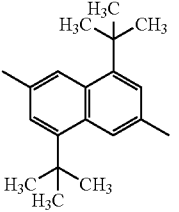 | 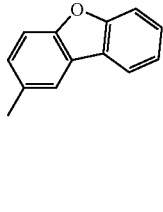 | 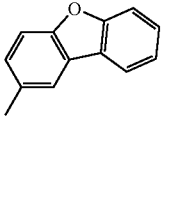 | 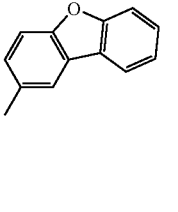 | 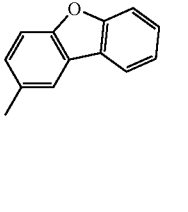 |
| D-58 | 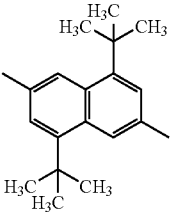 | 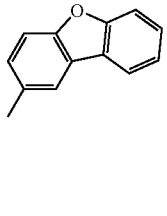 | 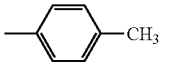 | 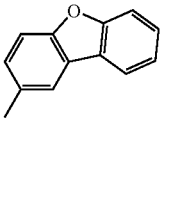 | 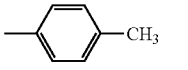 |
| D-59 | 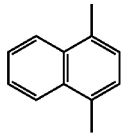 | 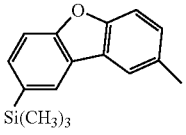 | 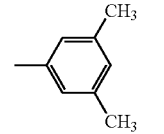 | 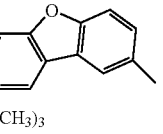 | 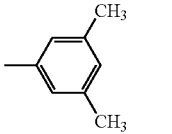 |
| D-60 | 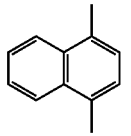 | 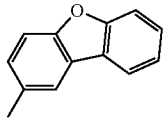 | 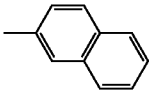 | 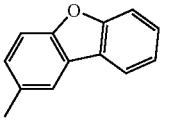 | 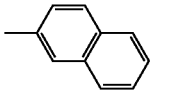 |
TABLE 7
| No | Ar₀ | Ar₁ | Ar₂ | Ar₃ | Ar₄ |
|---|---|---|---|---|---|
| D-61 | 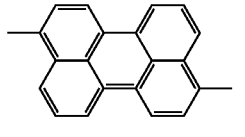 | 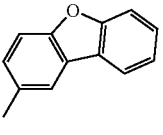 |  | 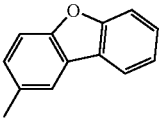 |  |
| D-62 | 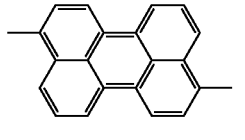 | 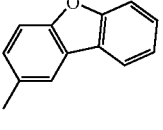 | 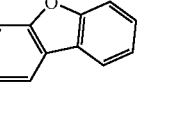 | 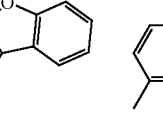 | 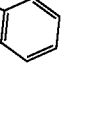 |
| D-63 | 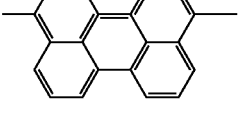 | 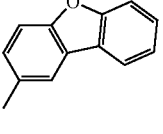 | 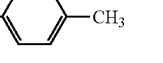 | 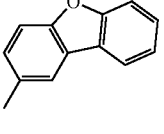 | 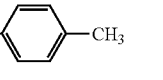 |

TABLE 7-continued

| No | Ar₀ | Ar₁ | Ar₂ | Ar₃ | Ar₄ |
|---|---|---|---|---|---|
| D-64 | perylene (structure) | dibenzofuran-Si(CH₃)₃ | 3,5-dimethylphenyl | dibenzofuran-Si(CH₃)₃ | 3,5-dimethylphenyl |
| D-65 | dimethylphenanthrene | methyldibenzofuran | methylnaphthyl | methyldibenzofuran | methylnaphthyl |
| D-66 | dimethylphenanthrene | methyldibenzofuran | phenyl | methyldibenzofuran | phenyl |
| D-67 | triphenyl-methyl-chrysene/tetracene | methyldibenzofuran | methyldibenzofuran | methyldibenzofuran | methyldibenzofuran |
| D-68 | triphenyl-methyl-chrysene/tetracene | methyldibenzofuran | 4-methylphenyl | methyldibenzofuran | 4-methylphenyl |
| D-69 | diphenyl-dimethyl-naphthalene | dibenzofuran-Si(CH₃)₃ | 3,5-dimethylphenyl | dibenzofuran-Si(CH₃)₃ | 3,5-dimethylphenyl |
| D-70 | diphenyl-dimethyl-naphthalene | methyldibenzofuran | methylnaphthyl | methyldibenzofuran | methylnaphthyl |

Next, a production method of the aromatic amine derivative of the present invention is described.

A method of producing the aromatic amine derivative represented by the general formula (1) of the present invention is not particularly limited, and it is sufficient that the aromatic amine derivative be produced by a known method. For example, the aromatic amine derivative is produced by aminating 6,12-dibromochrysene obtained by the method described in Rev. Roum. Chim., 34, p. 1907 (1989) (M. D. Bancia et al.) with a diarylamine.

The aromatic amine derivative of the present invention is suitably used as a material for an organic EL device, and is particularly preferably used as a light emitting material. The aromatic amine derivative is suitably used as a blue light emitting material or a green light emitting material.

In addition, the aromatic amine derivative of the present invention is suitably used also as a doping material for an organic EL device.

An organic EL device of the present invention is a device in which an organic thin film layer formed of one or more layers is formed between an anode and a cathode. When the device is of a one-layer type, a light emitting layer is provided between the anode and the cathode. The light emitting layer contains a light emitting material, and may contain a hole injecting material or an electron injecting material in addition to the light emitting material in order that a hole injected from the anode or an electron injected from the cathode may be transported to the light emitting material. The aromatic amine derivative of the present invention may be used as a light emitting material or doping material in a light emitting layer because the aromatic amine derivative has a high light emitting characteristic, an excellent hole injecting characteristic, an excellent hole transporting characteristic, an excellent electron injecting characteristic, and an excellent electron transporting characteristic.

In the organic EL device of the present invention, the light emitting layer preferably contains the aromatic amine derivative of the present invention, and the content is preferably 0.1 to 20 mass, or more preferably 1 to 10 mass % in ordinary cases. In addition, the light emitting layer may be formed only of the aromatic amine derivative of the present invention because the aromatic amine derivative brings together extremely high fluorescent quantum efficiency, a high hole transporting ability, and a high electron transporting ability, and enables the formation of a uniform thin film.

In addition, the organic EL device of the present invention is preferably an organic EL device having an organic thin film layer formed of two or more layers including at least a light emitting layer and interposed between a cathode and an anode in which an organic layer mainly formed of the aromatic amine derivative of the present invention is placed between the anode and the light emitting layer. Examples of the organic layer include a hole injecting layer and a hole transporting layer.

Further, when the aromatic amine derivative of the present invention is contained as a doping material, it is preferred to contain at least one kind selected from an anthracene derivative represented by the following general formula (i) and a pyrene derivative represented by the following general formula (ii).

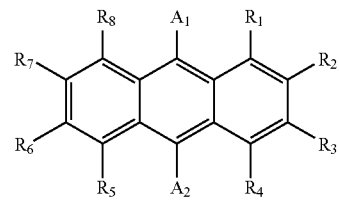

In the general formula (i), $A_1$ and $A_2$ each independently represent a group derived from a substituted or unsubstituted aromatic ring having 6 to 20 ring-forming carbon atoms. The aromatic ring may be substituted with one or two or more substituents. The substituent for the aromatic ring is selected from, a substituted or unsubstituted aryl group having 6 to 50 carbon atoms, a substituted or unsubstituted alkyl group having 1 to 50 carbon atoms, a substituted or unsubstituted cycloalkyl group having 3 to 50 carbon atoms, a substituted or unsubstituted alkoxy group having 1 to 50 carbon atoms, a substituted or unsubstituted aralkyl group (the aryl portion having 6 to 50 carbon atoms and the alkyl portion having 1 to 5 carbon atoms), a substituted or unsubstituted aryloxy group having 6 to 50 carbon atoms, a substituted or unsubstituted arylthio group having 6 to 50 carbon atoms, a substituted or unsubstituted alkoxycarbonyl group (the alkoxy portion having 1 to 50 carbon atoms), a substituted or unsubstituted silyl group, a carboxyl group, a halogen atom, a cyano group, a nitro group, and a hydroxyl group. Specific examples of the groups represented in $R^5$ to $R^{12}$ are described below. When the aromatic ring is substituted with two or more substituents, the substituents may be identical to or different from each other. Substituents adjacent to each other may be bonded to each other to form a saturated or unsaturated cyclic structure. $A_1$ and $A_2$ are preferably different from each other. In addition, at least one of $A_1$ and $A_2$ preferably represents a substituent having a substituted or unsubstituted fused ring group having 10 to 30 carbon atoms, or more preferably represents a substituent having a substituted or unsubstituted naphthyl group.

Examples of the substituted or unsubstituted group derived from an aromatic ring having 6 to 20 ring-forming carbon atoms represented by any one of $A_1$ and $A_2$ include a phenyl group, a 1-naphthyl group, a 2-naphthyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, an m-terphenyl-4-yl group, an m-terphenyl-3-yl group, an m-terphenyl-2-yl group, an o-tolyl group, an m-tolyl group, a p-tolyl group, a p-t-butylphenyl group, a p-(2-phenylpropyl)phenyl group, a 3-methyl-2-naphthyl group, a 4-methyl-1-naphthyl group, a 4-methyl-1-anthryl group, a 4'-methylbiphenylyl group, and a 4''-t-butyl-p-terphenyl-4-yl group. The group is preferably a group derived from a substituted or unsubstituted aromatic ring having 10 to 14 ring-forming carbon atoms, or particularly preferably a 1-naphthyl group, a 2-naphthyl group, or a 9-phenanthryl group.

$R_1$ to $R_8$ each independently represent a group selected from a hydrogen atom, a substituted or unsubstituted aryl group having 6 to 50 ring-forming carbon atoms, a substituted or unsubstituted heteroaryl group having 4 to 50 ring-forming atoms, a substituted or unsubstituted alkyl group having 1 to 50 carbon atoms, a substituted or unsubstituted cycloalkyl group having 3 to 50 ring-forming carbon atoms, a substituted or unsubstituted alkoxy group having 1 to 50 carbon atoms, a substituted or unsubstituted aralkyl group having 7 to 50 ring-forming carbon atoms, a substituted or unsubstituted aryloxy group having 6 to 50 ring-forming carbon atoms, a substituted or unsubstituted arylthio group having 6 to 50 ring-forming carbon atoms, a substituted or unsubstituted alkoxycarbonyl group having 1 to 50 carbon atoms, a substituted or unsubstituted silyl group, a carboxyl group, a halogen atom, a cyano group, a nitro group, and a hydroxyl group.

Examples of the substituted or unsubstituted aryl group having 6 to 50 ring-forming carbon atoms represented by any one of $R_1$ to $R_8$ include a phenyl group, a 1-naphthyl group, a 2-naphthyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, an m-terphenyl-4-yl group, an m-terphenyl-3-yl group, an m-terphenyl-2-yl group, an o-tolyl group, an m-tolyl group, a p-tolyl group, a p-t-butylphenyl group, a p-(2-phenylpropyl) phenyl group, a 3-methyl-2-naphthyl group, a 4-methyl-1-naphthyl group, a 4-methyl-1-anthryl group, a 4'-methylbiphenylyl group, and a 4"-t-butyl-p-terphenyl-4-yl group.

Examples of the substituted or unsubstituted heteroaryl group having 4 to 50 ring-forming atoms represented by any one of $R_1$ to $R_8$ include a 1-pyrrolyl group, a 2-pyrrolyl group, a 3-pyrrolyl group, a pyrazinyl group, a 2-pyridinyl group, a 3-pyridinyl group, a 4-pyridinyl group, a 1-indolyl group, a 2-indolyl group, a 3-indolyl group, a 4-indolyl group, a 5-indolyl group, a 6-indolyl group, a 7-indolyl group, a 1-isoindolyl group, a 2-isoindolyl group, a 3-isoindolyl group, a 4-isoindolyl group, a 5-isoindolyl group, a 6-isoindolyl group, a 7-isoindolyl group, a 2-furyl group, a 3-furyl group, a 2-benzofuranyl group, a 3-benzofuranyl group, a 4-benzofuranyl group, a 5-benzofuranyl group, a 6-benzofuranyl group, a 7-benzofuranyl group, a 1-isobenzofuranyl group, a 3-isobenzofuranyl group, a 4-isobenzofuranyl group, a 5-isobenzofuranyl group, a 6-isobenzofuranyl group, a 7-isobenzofuranyl group, a quinolyl group, a 3-quinolyl group, a 4-quinolyl group, a 5-quinolyl group, a 6-quinolyl group, a 7-quinolyl group, an 8-quinolyl group, a 1-isoquinolyl group, a 3-isoquinolyl group, a 4-isoquinolyl group, a 5-isoquinolyl group, a 6-isoquinolyl group, a 7-isoquinolyl group, an 8-isoquinolyl group, a 2-quinoxalinyl group, a 5-quinoxalinyl group, a 6-quinoxalinyl group, a 1-carbazolyl group, a 2-carbazolyl group, a 3-carbazolyl group, a 4-carbazolyl group, a 9-carbazolyl group, a 1-phenanthridinyl group, a 2-phenanthridinyl group, a 3-phenanthridinyl group, a 4-phenanthridinyl group, a 6-phenanthridinyl group, a 7-phenanthridinyl group, an 8-phenanthridinyl group, a 9-phenanthridinyl group, a 10-phenanthridinyl group, a 1-acridinyl group, a 2-acridinyl group, a 3-acridinyl group, a 4-acridinyl group, a 9-acridinyl group, a 1,7-phenanthrolin-2-yl group, a 1,7-phenanthrolin-3-yl group, a 1,7-phenanthrolin-4-yl group, a 1,7-phenanthrolin-5-yl group, a 1,7-phenanthrolin-6-yl group, a 1,7-phenanthrolin-8-yl group, a 1,7-phenanthrolin-9-yl group, a 1,7-phenanthrolin-10-yl group, a 1,8-phenanthrolin-2-yl group, a 1,8-phenanthrolin-3-yl group, a 1,8-phenanthrolin-4-yl group, a 1,8-phenanthrolin-5-yl group, a 1,8-phenanthrolin-6-yl group, a 1,8-phenanthrolin-7-yl group, a 1,8-phenanthrolin-9-yl group, a 1,8-phenanthrolin-10-yl group, a 1,9-phenanthrolin-2-yl group, a 1,9-phenanthrolin-3-yl group, a 1,9-phenanthrolin-4-yl group, a 1,9-phenanthrolin-5-yl group, a 1,9-phenanthrolin-6-yl group, a 1,9-phenanthrolin-7-yl group, a 1,9-phenanthrolin-8-yl group, a 1,9-phenanthrolin-10-yl group, a 1,10-phenanthrolin-2-yl group, a 1,10-phenanthrolin-3-yl group, a 1,10-phenanthrolin-4-yl group, a 1,10-phenanthrolin-5-yl group, a 2,9-phenanthrolin-1-yl group, a 2,9-phenanthrolin-3-yl group, a 2,9-phenanthrolin-4-yl group, a 2,9-phenanthrolin-5-yl group, a 2,9-phenanthrolin-6-yl group, a 2,9-phenanthrolin-7-yl group, a 2,9-phenanthrolin-8-yl group, a 2,9-phenanthrolin-10-yl group, a 2,8-phenanthrolin-1-yl group, a 2,8-phenanthrolin-3-yl group, a 2,8-phenanthrolin-4-yl group, a 2,8-phenanthrolin-5-yl group, a 2,8-phenanthrolin-6-yl group, a 2,8-phenanthrolin-7-yl group, a 2,8-phenanthrolin-9-yl group, a 2,8-phenanthrolin-10-yl group, a 2,7-phenanthrolin-1-yl group, a 2,7-phenanthrolin-3-yl group, a 2,7-phenanthrolin-4-yl group, a 2,7-phenanthrolin-5-yl group, a 2,7-phenanthrolin-6-yl group, a 2,7-phenanthrolin-8-yl group, a 2,7-phenanthrolin-9-yl group, a 2,7-phenanthrolin-10-yl group, a 1-phenazinyl group, a 2-phenazinyl group, a 1-phenothiazinyl group, a 2-phenothiazinyl group, a 3-phenothiazinyl group, a 4-phenothiazinyl group, a 10-phenothiazinyl group, a 1-phenoxazinyl group, a 2-phenoxazinyl group, a 3-phenoxazinyl group, a 4-phenoxazinyl group, a 10-phenoxazinyl group, a 2-oxazolyl group, a 4-oxazolyl group, a 5-oxazolyl group, a 2-oxadiazolyl group, a 5-oxadiazolyl group, a 3-furazanyl group, a 2-thienyl group, a 3-thienyl group, a 2-methylpyrrol-1-yl group, a 2-methylpyrrol-3-yl group, a 2-methylpyrrol-4-yl group, a 2-methylpyrrol-5-yl group, a 3-methylpyrrol-1-yl group, a 3-methylpyrrol-2-yl group, a 3-methylpyrrol-4-yl group, a 3-methylpyrrol-5-yl group, a 2-t-butylpyrrol-4-yl group, a 3-(2-phenylpropyl)pyrrol-1-yl group, a 2-methyl-1-indolyl group, a 4-methyl-1-indolyl group, a 2-methyl-3-indolyl group, a 4-methyl-3-indolyl group, a 2-t-butyl-1-indolyl group, a 4-t-butyl-1-indolyl group, a 2-t-butyl-3-indolyl group, and a 4-t-butyl-3-indolyl group.

Examples of the substituted or unsubstituted alkyl group having 1 to 50 carbon atoms represented by any one of $R_1$ to $R_8$ include a methyl group, an ethyl group, a propyl group, an isopropyl group, an n-butyl group, an s-butyl group, an isobutyl group, a t-butyl group, an n-pentyl group, an n-hexyl group, an n-heptyl group, an n-octyl group, a hydroxymethyl group, a 1-hydroxyethyl group, a 2-hydroxyethyl group, a 2-hydroxyisobutyl group, a 1,2-dihydroxyethyl group, a 1,3-dihydroxyisopropyl group, a 2,3-dihydroxy-t-butyl group, a 1,2,3-trihydroxypropyl group, a chloromethyl group, a 1-chloroethyl group, a 2-chloroethyl group, a 2-chloroisobutyl group, a 1,2-dichloroethyl group, a 1,3-dichloroisopropyl group, a 2,3-dichloro-t-butyl group, a 1,2,3-trichloropropyl group, a bromomethyl group, a 1-bromoethyl group, a 2-bromoethyl group, a 2-bromoisobutyl group, a 1,2-dibromoethyl group, a 1,3-dibromoisopropyl group, a 2,3-dibromo-t-butyl group, a 1,2,3-tribromopropyl group, an iodomethyl group, a 1-iodoethyl group, a 2-iodoethyl group, a 2-iodoisobutyl group, a 1,2-diiodoethyl group, a 1,3-diiodoisopropyl group, a 2,3-diiodo-t-butyl group, a 1,2,3-triiodopropyl group, an aminomethyl group, a 1-aminoethyl group, a 2-aminoethyl group, a 2-aminoisobutyl group, a 1,2-diaminoethyl group, a 1,3-diaminoisopropyl group, a 2,3-diamino-t-butyl group, a 1,2,3-triaminopropyl group, a cyanomethyl group, a 1-cyanoethyl group, a 2-cyanoethyl group, a 2-cyanoisobutyl group, a 1,2-dicyanoethyl group, a 1,3-dicyanoisopropyl group, a 2,3-dicyano-t-butyl group, a 1,2,3-tricyanopropyl group, a nitromethyl group, a 1-nitroethyl group, a 2-nitroethyl group, a 2-nitroisobutyl group, a 1,2-dinitroethyl group, a 1,3-dinitroisopropyl group, a 2,3-dinitro-t-butyl group, and a 1,2,3-trinitropropyl group.

Examples of the substituted or unsubstituted cycloalkyl group having 3 to 50 ring-forming carbon atoms represented by any one of $R_1$ to $R_8$ or as the substituent on the aromatic ring include a cyclopropyl group, a cyclobutyl group, a cyclopentyl group, a cyclohexyl group, a 4-methylcyclohexyl group, a 1-adamantyl group, a 2-adamantyl group, a 1-norbornyl group, and a 2-norbornyl group.

The substituted or unsubstituted alkoxy group having 1 to 50 carbon atoms represented by any one of $R_1$ to $R_8$ is a group represented as —OZ, and Z is selected from the substituted or unsubstituted alkyl groups each having 1 to 50 carbon atoms represented by $R_1$ to $R_8$.

Examples of the substituted or unsubstituted aralkyl group having 7 to 50 ring-forming carbon atoms (the aryl portion having 6 to 50 carbon atoms and the alkyl portion having 1 to 50 carbon atoms) as the substituents represented by any one of $R_1$ to $R_8$ include a benzyl group, a 1-phenylethyl group, a 2-phenylethyl group, a 1-phenylisopropyl group, a 2-phenylisopropyl group, a phenyl-t-butyl group, an α-naphthylmethyl group, a 1-α-naphthylethyl group, a 2-α-naphthylethyl group, a 1-α-naphthylisopropyl group, a 2-α-naphthylisopropyl group, a β-naphthylmethyl group, a 1-β-naphthylethyl group, a 2-β-naphthylethyl group, a 1-β-naphthylisopropyl group, a 2-β-naphthylisopropyl group, a 1-pyrrolylmethyl group, a 2-(1-pyrrolyl)ethyl group, a p-methylbenzyl group, an m-methylbenzyl group, an o-methylbenzyl group, a p-chlorobenzyl group, an m-chlorobenzyl group, an o-chlorobenzyl group, a p-bromobenzyl group, an m-bromobenzyl group, an o-bromobenzyl group, a p-iodobenzyl group, an m-iodobenzyl group, an o-iodobenzyl group, a p-hydroxybenzyl group, an m-hydroxybenzyl group, an o-hydroxybenzyl group, a p-aminobenzyl group, an m-aminobenzyl group, an o-aminobenzyl group, a p-nitrobenzyl group, an m-nitrobenzyl group, an o-nitrobenzyl group, a p-cyanobenzyl group, an m-cyanobenzyl group, an o-cyanobenzyl group, a 1-hydroxy-2-phenylisopropyl group, and a 1-chloro-2-phenylisopropyl group.

The substituted or unsubstituted aryloxy group having 6 to 50 ring-forming carbon atoms and the substituted or unsubstituted arylthio group having 6 to 50 ring-forming carbon atoms each represented by any one of $R_1$ to $R_8$ are represented as —OY and —SY, respectively. Each Y is selected from the substituted or unsubstituted aryl groups having 6 to 50 atoms represented by any one of $R_1$ to $R_8$.

The substituted or unsubstituted alkoxycarbonyl group having 1 to 50 carbon atoms represented by any one of $R_1$ to $R_8$ is represented as —COOZ. Z is selected from the substituted or unsubstituted alkyl groups having 1 to 50 carbon atoms represented by any one of $R_1$ to $R_8$.

Examples of the substituted silyl group represented by any one of $R_1$ to $R_8$ include a trimethylsilyl group, a triethylsilyl group, a t-butyldimethylsilyl group, a vinyldimethylsilyl group, a propyldimethylsilyl group, and a triphenylsilyl group.

Examples of the halogen atom represented by any one of $R_1$ to $R_8$ include fluorine, chlorine, bromine, and iodine.

The substituent on an aromatic ring represented by any one of $R_1$ to $R_8$ and/or $A_1$ and $A_2$ may be further substituted by a halogen atom, a hydroxyl group, a nitro group, a cyano group, an alkyl group, an aryl group, a cycloalkyl group, an alkoxy group, an aromatic heterocyclic group, an aralkyl group, an aryloxy group, an arylthio group, an alkoxycarbonyl group, a carboxyl group, or the like.

In the general formula (1), $A_1$ and $A_2$ preferably represent different groups.

The anthracene derivative represented by the general formula (i) is preferably a compound having a structure represented by the following general formula (i'):

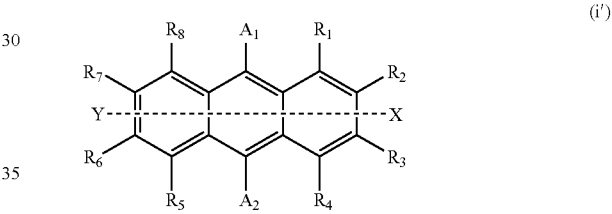

(i')

(in the formula, $A_1$ and $A_2$, and $R_1$ to $R_8$ are as defined in the formula (i), provided that the substituents $A_1$ and $A_2$ at the 9- and 10-positions of the anthracene structure are asymmetric with respect to the X-Y axis.)

Specific examples of the anthracene derivative represented by the general formula (i) to be used in the organic EL device of the present invention include various known anthracene derivatives such as an anthracene derivative having two anthracene skeletons in its molecule described in paragraphs [0043] to [0063] of JP 2009-356033 A and a compound having one anthracene skeleton described in p. 27 and 28 of WO 2005/061656 A1. Representative specific examples are shown below.

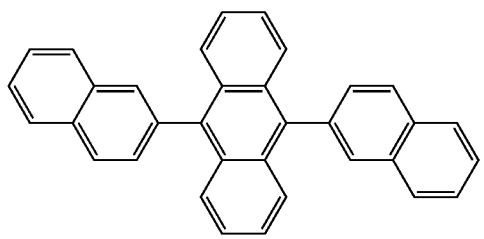

2a-1

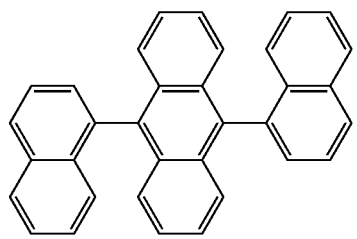

2a-2

2a-3
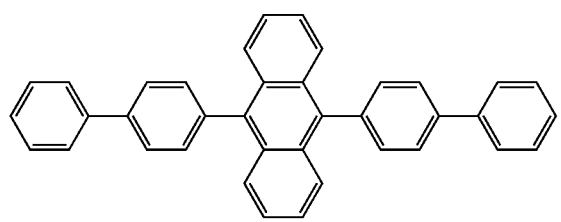
2a-4
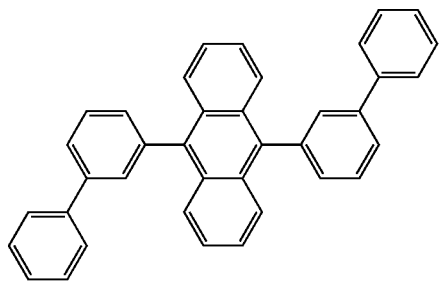
2a-5
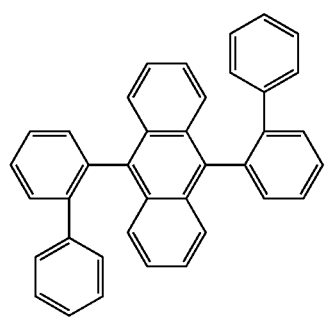
2a-6
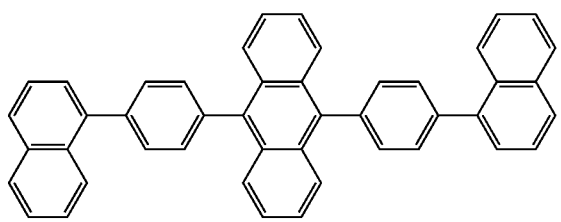
2a-7
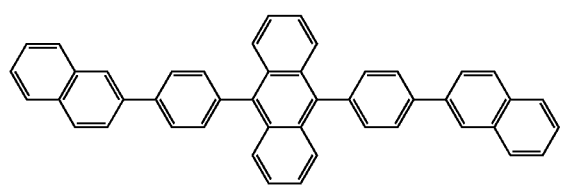
2a-8
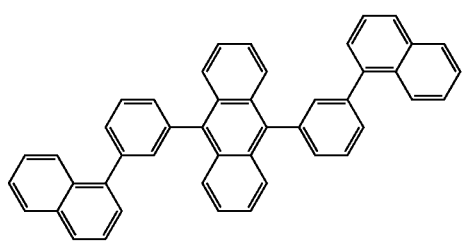
2a-9
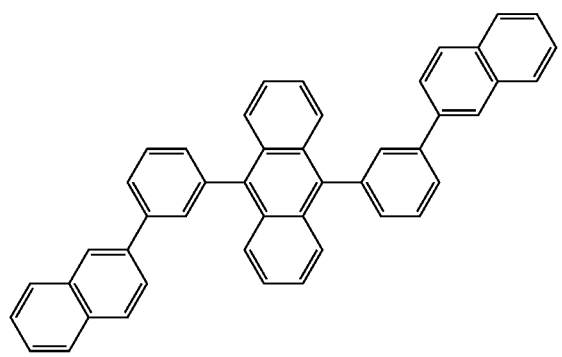
2a-10
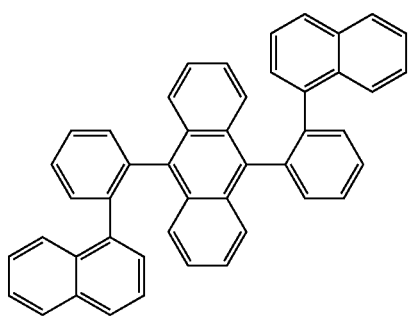

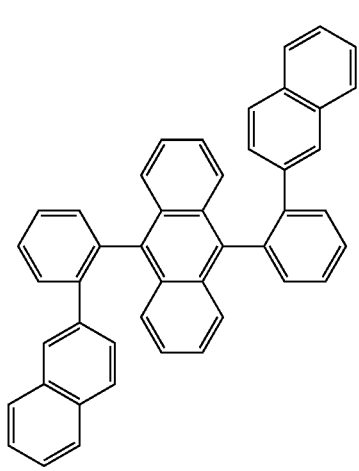

2a-18
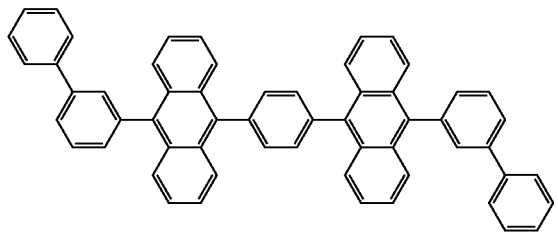
2a-19
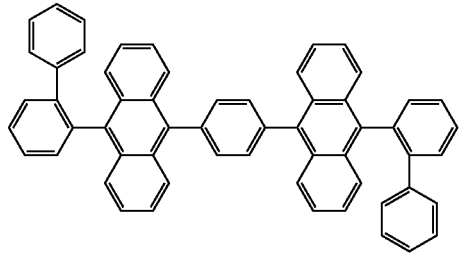
2a-20
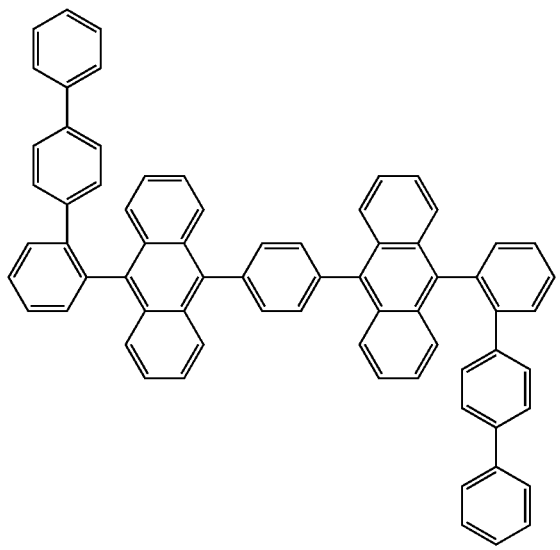
2a-21
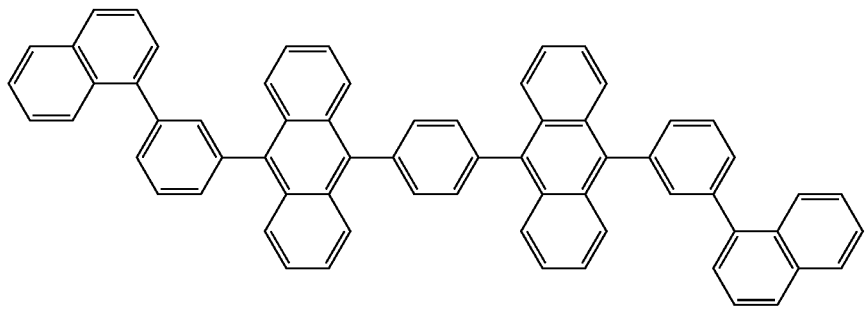
2a-22
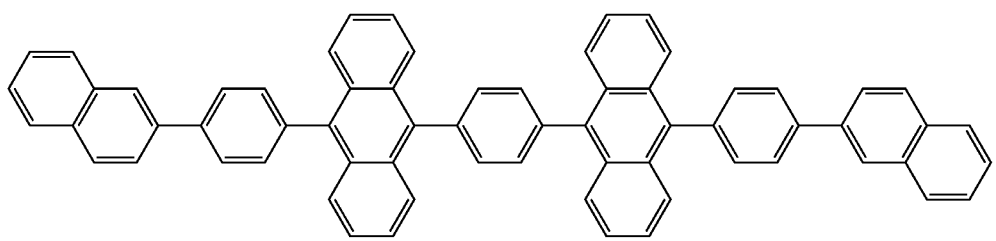

2a-23
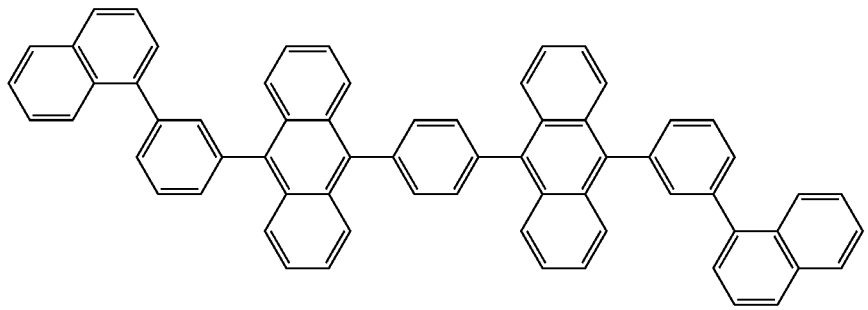
2a-24
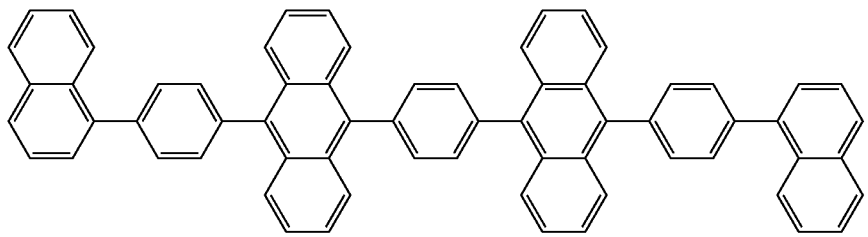
2a-25 2a-26
2a-27 2a-28
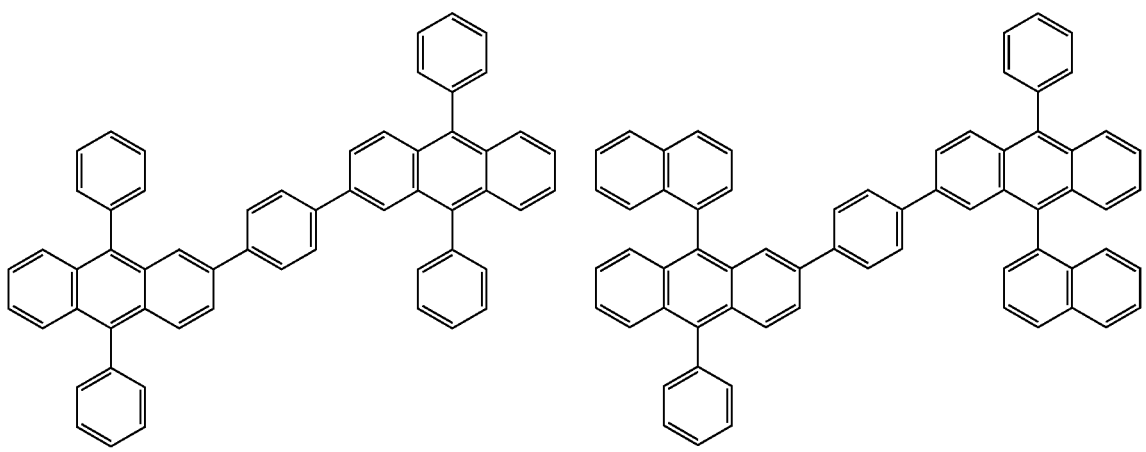
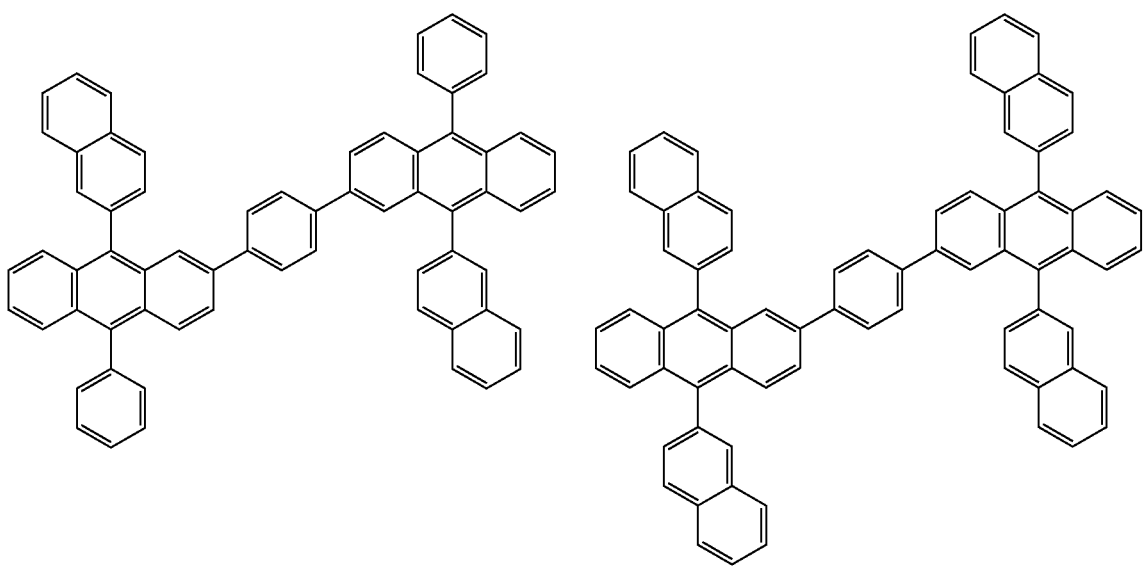

-continued
2a-29
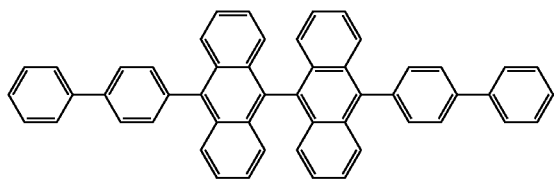
2a-30
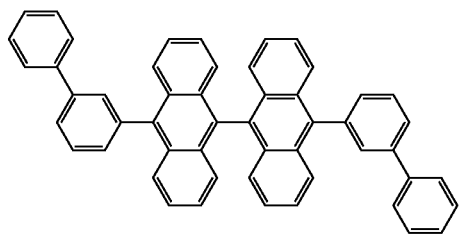
2a-31
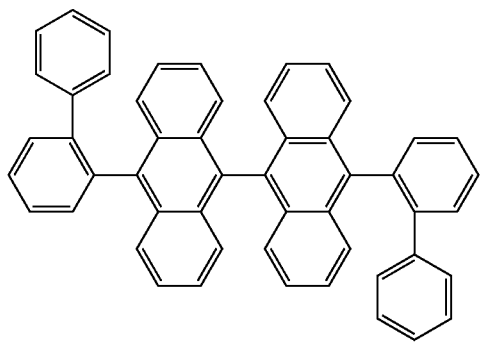
2a-32
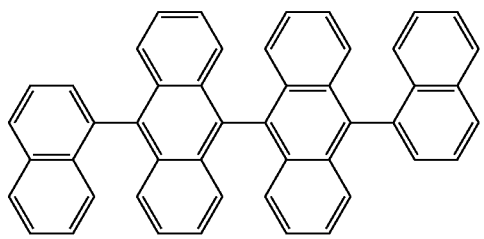
2a-33
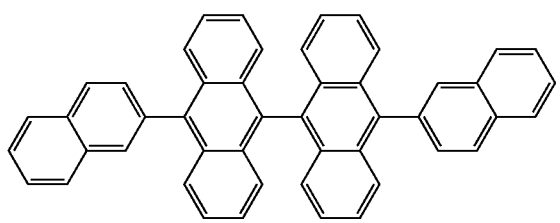
2a-34
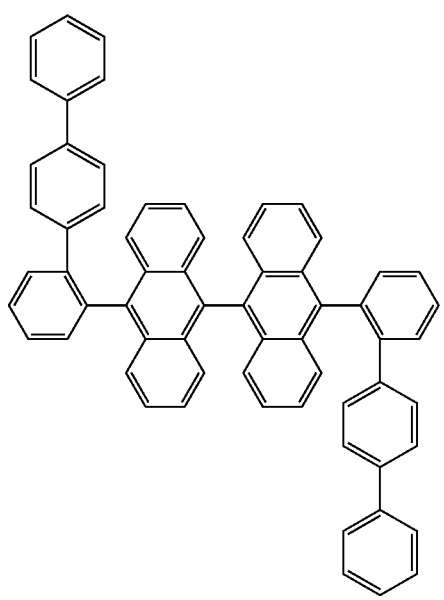
2a-35
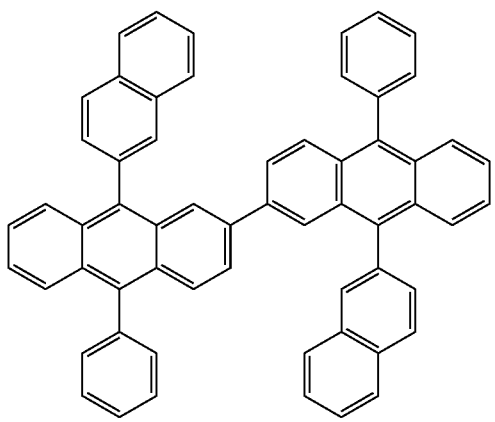
2a-36
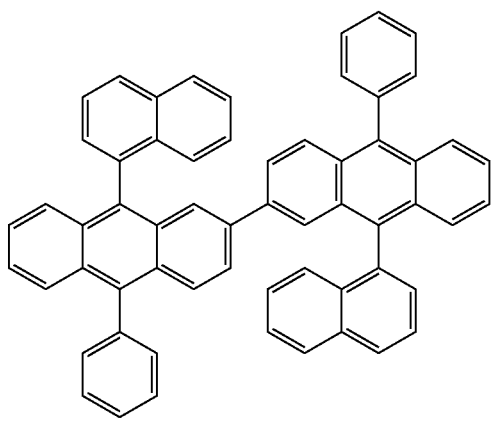

-continued
2a-37
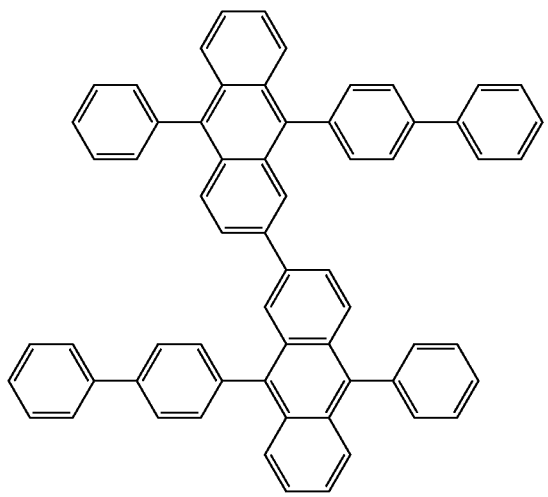
2a-38
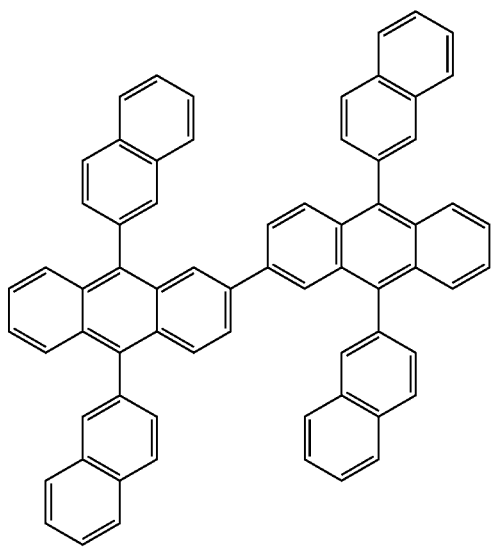
2a-39
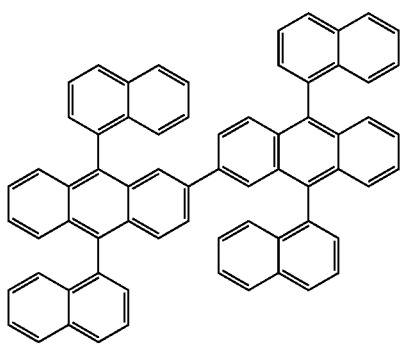
2a-40
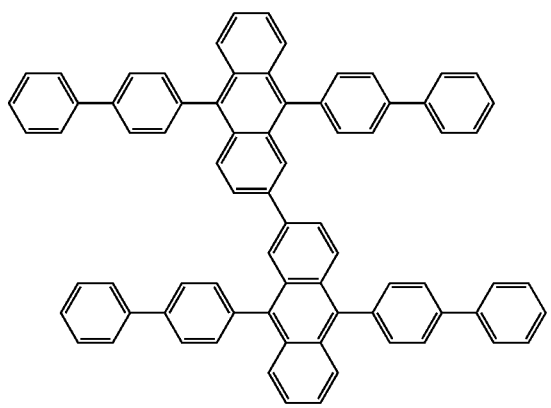
2a-41
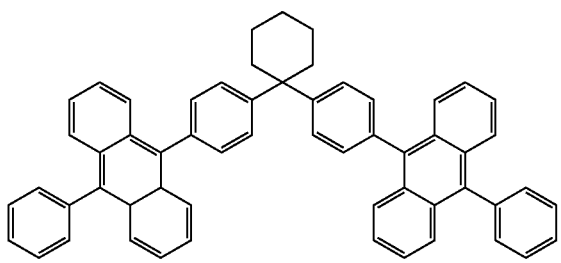
2a-42
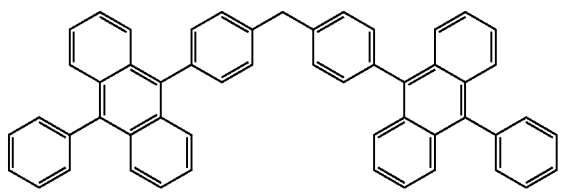
2a-43
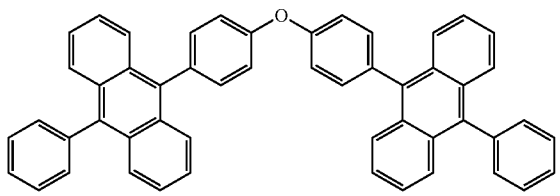
2a-44
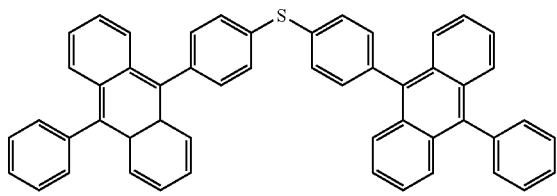

2a-45
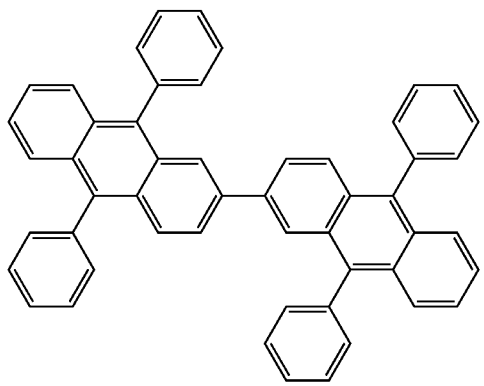
2a-46
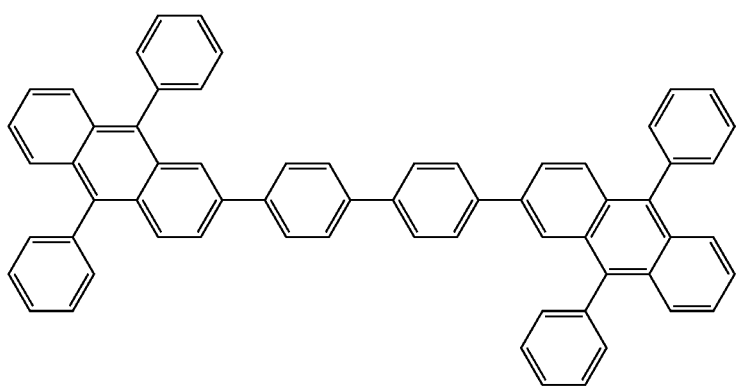
2a-47
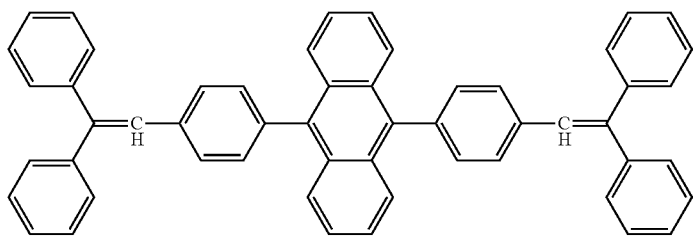
2a-48
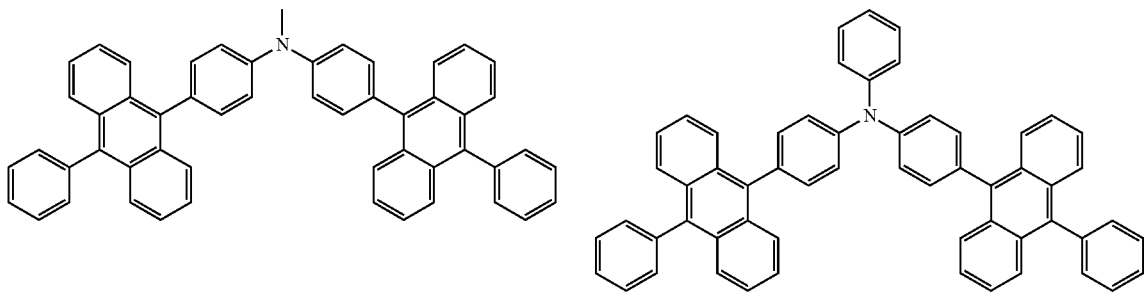
2a-49
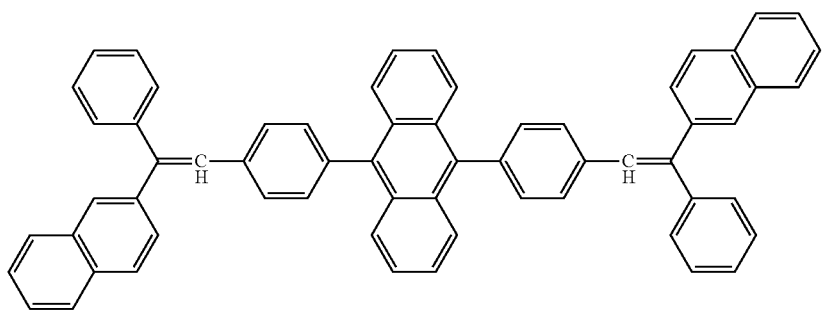
2a-50

2a'-51
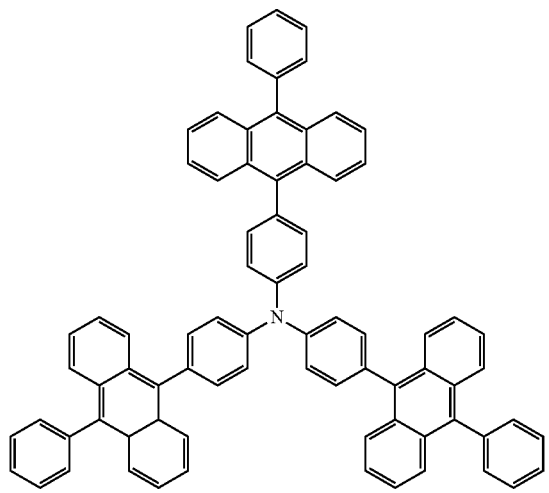
2a'-52
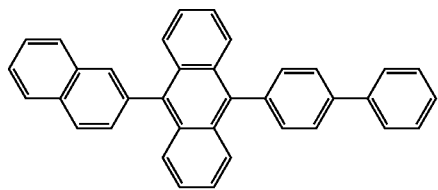
2a'-53
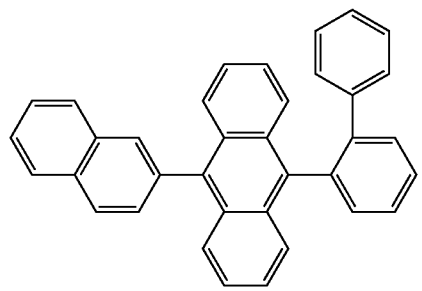
2a'-54
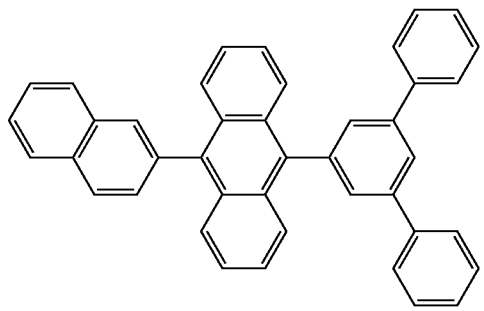
2a'-55
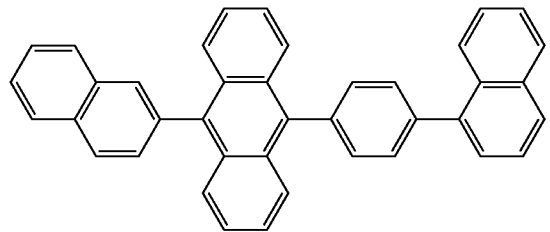
2a'-56
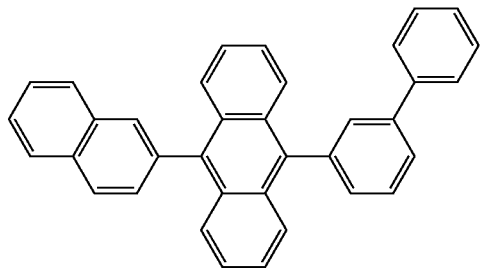
2a'-57
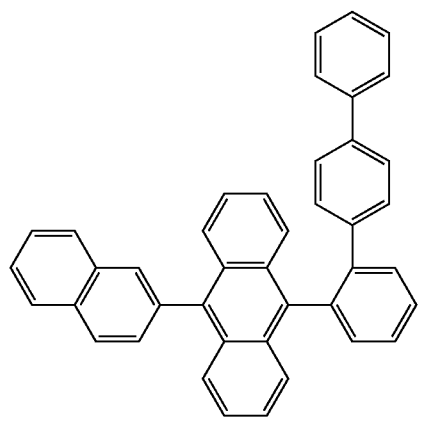
2a'-58
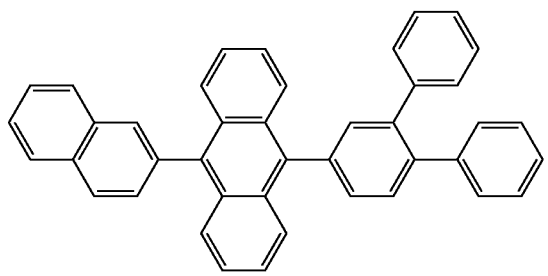

2a'-59
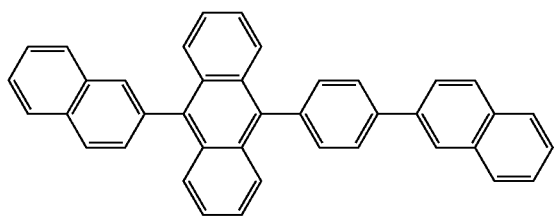
2a'-60
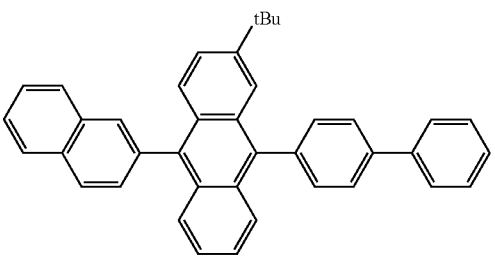
2a'-61
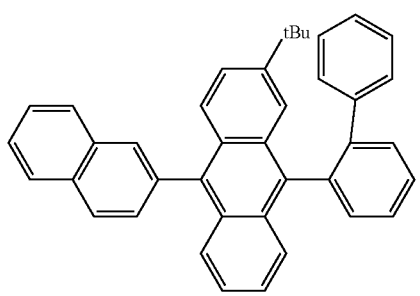
2a'-62
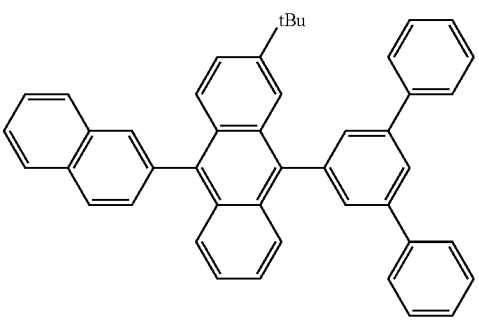
2a'-63
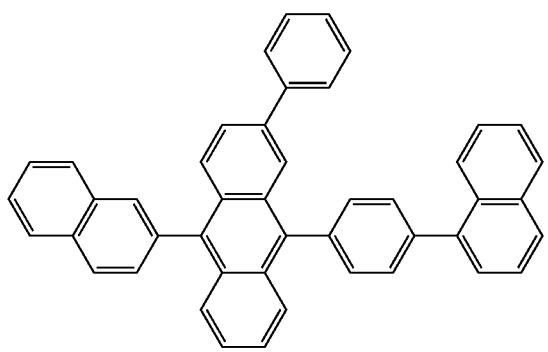
2a'-64
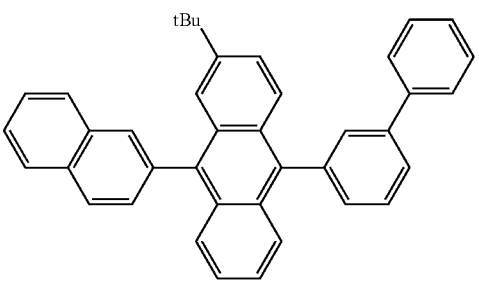
2a'-65
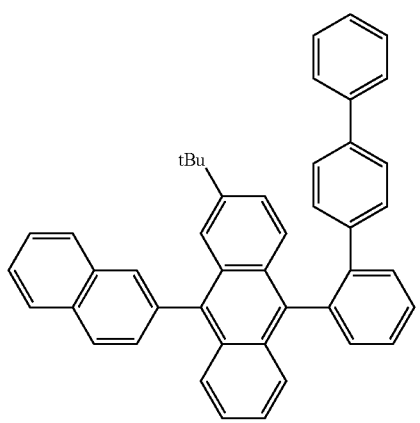
2a'-66
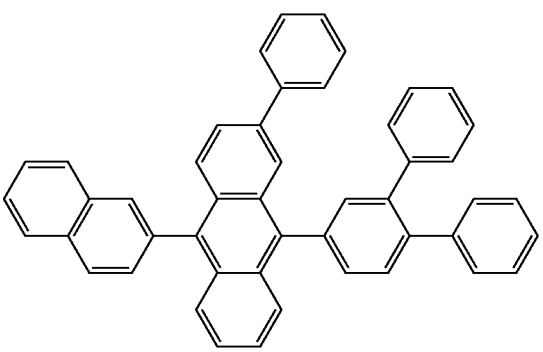

-continued
2a'-67
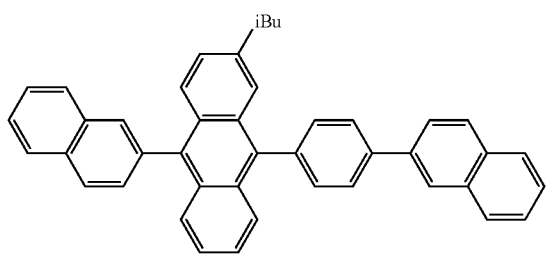
2a'-68
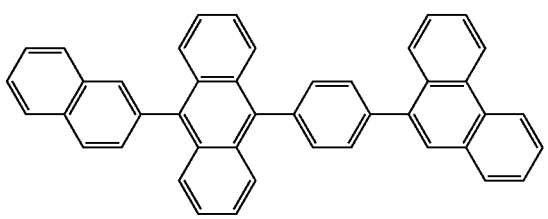
2a'-69
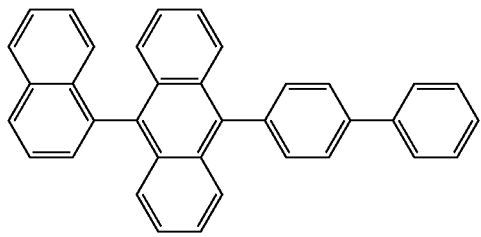
2a'-70
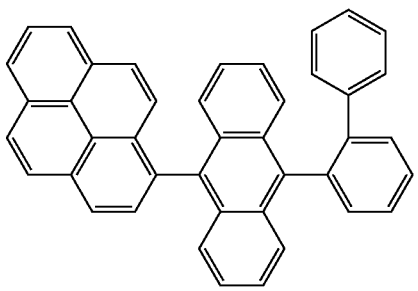
2a'-71
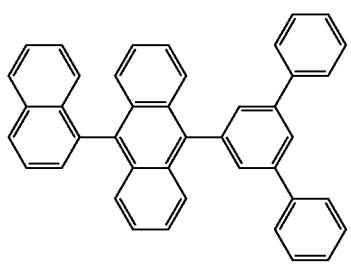
2a'-72
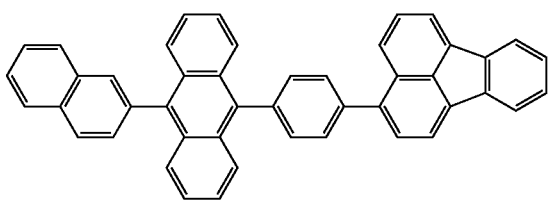
2a'-73
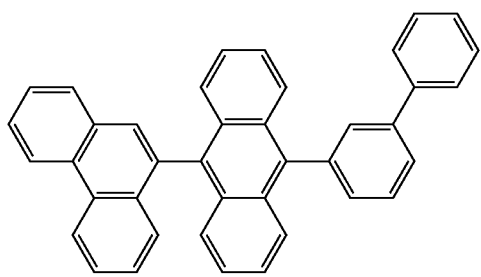
2a'-74
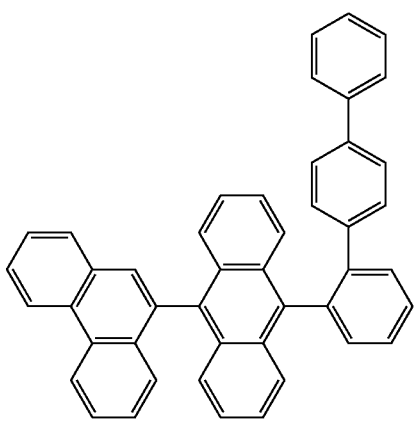
2a'-75
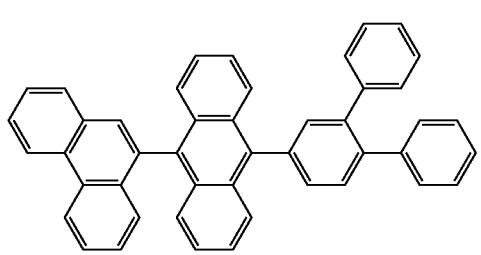
2a'-76
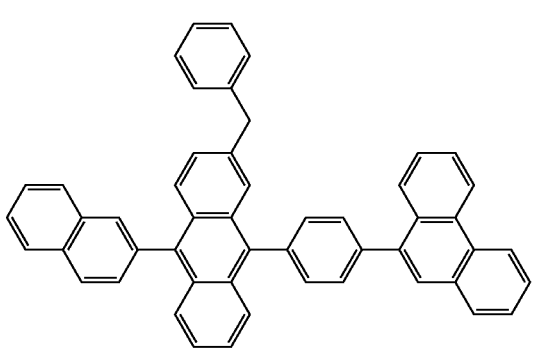

-continued
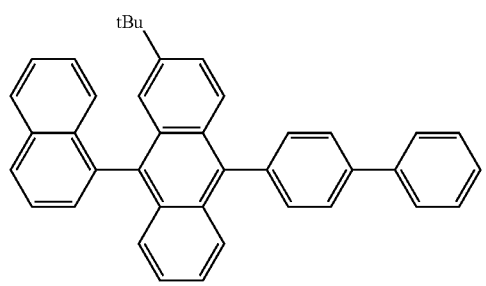
2a'-77
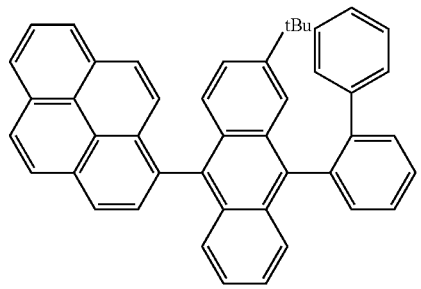
2a'-78
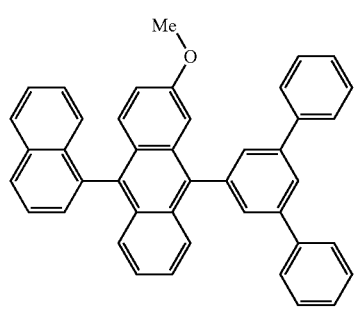
2a'-79
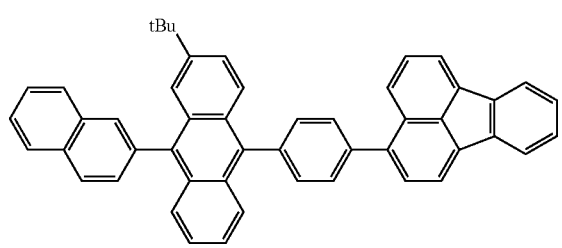
2a'-80
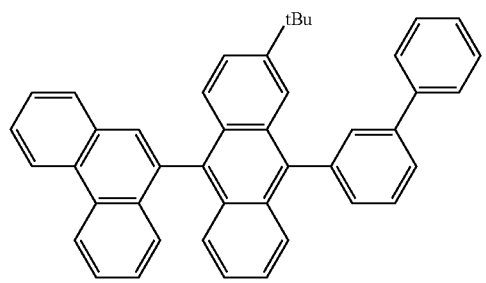
2a'-81
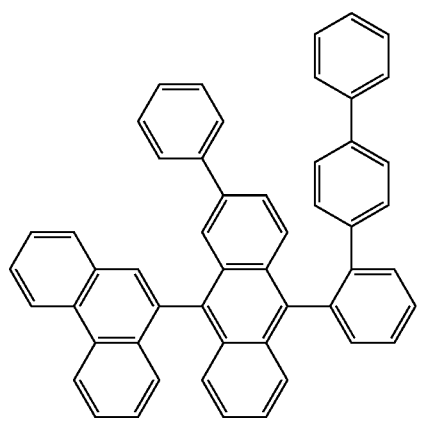
2a'-82
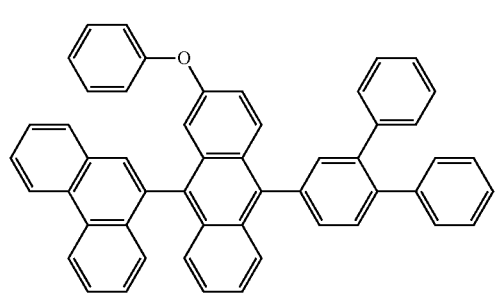
2a'-83
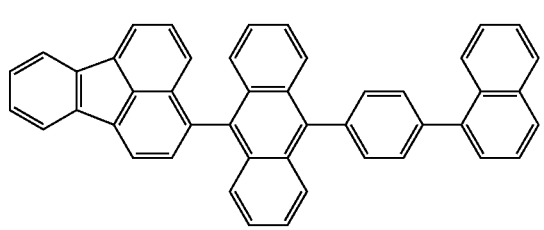
2a'-84

-continued
2a′-85
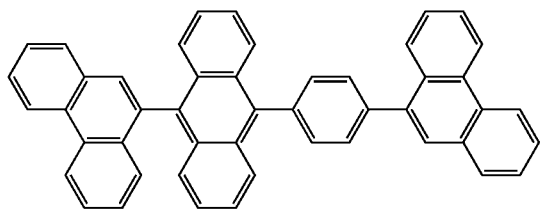
2a′-86
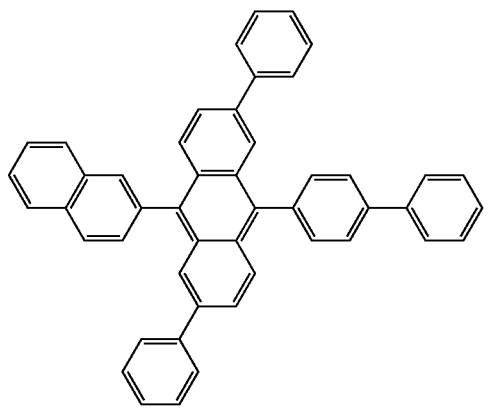
2a′-87
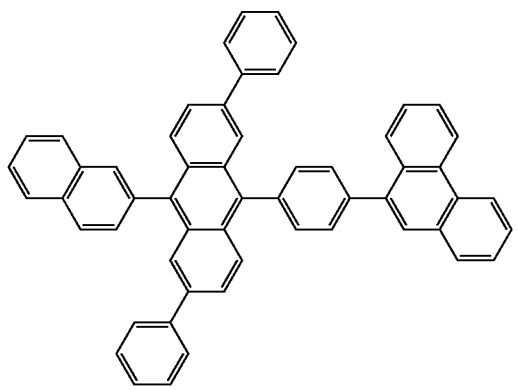
2a′-88
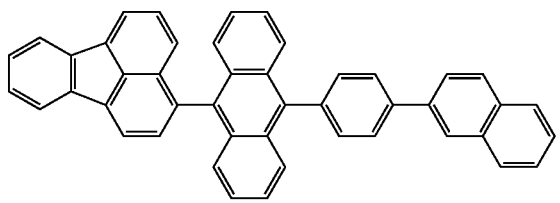
2a′-89
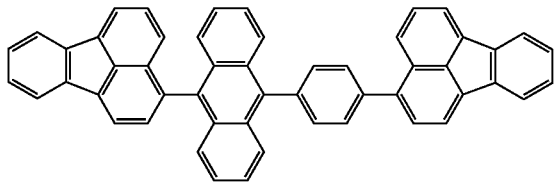
2a′-90
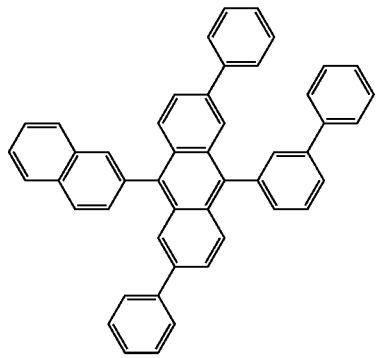
2a′-91
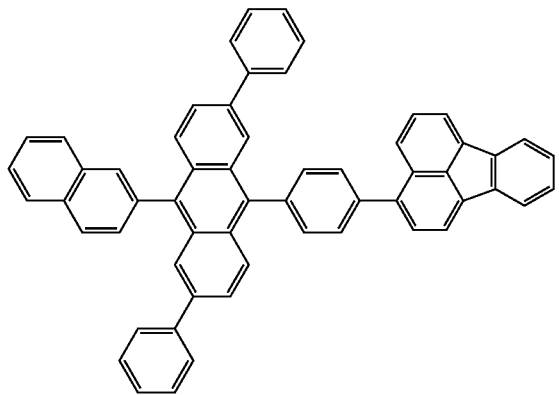
2a′-92
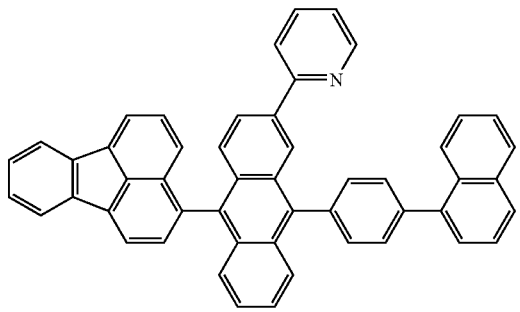

-continued
2a'-93
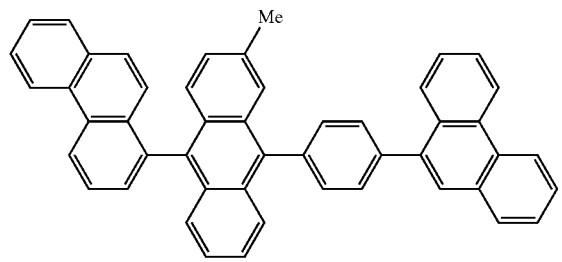
2a'-94
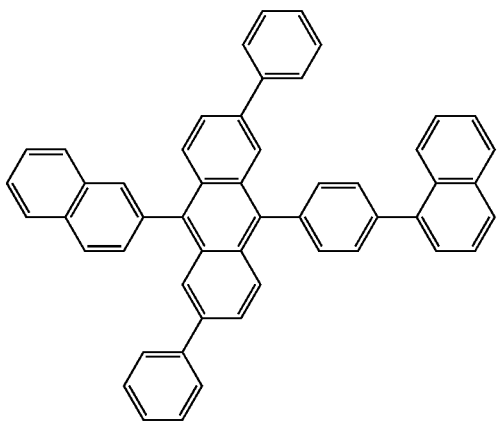
2a'-95
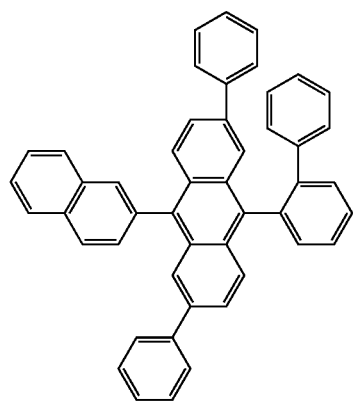
2a'-96
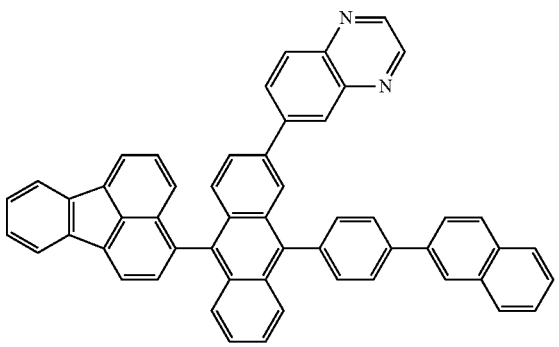
2a'-97
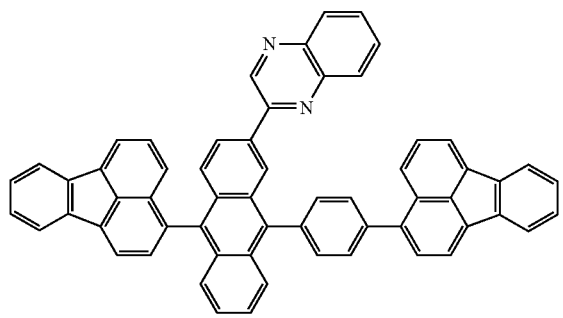
2a'-98
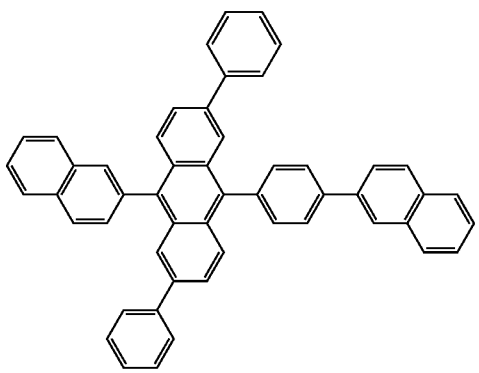

-continued
2a'-99
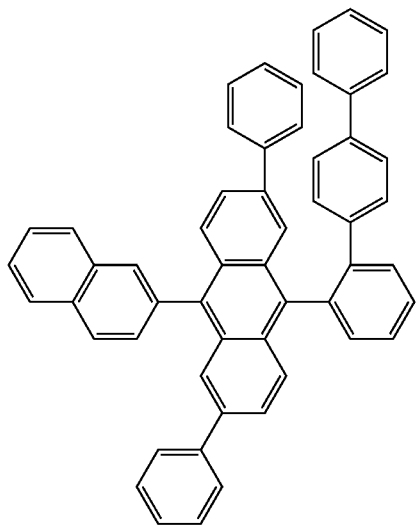
2a'-100
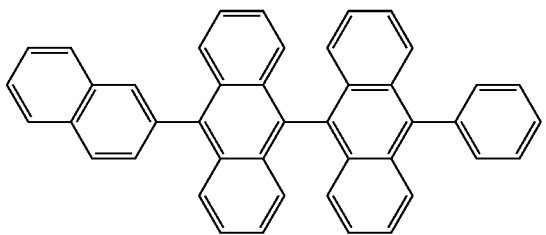
2a'-101
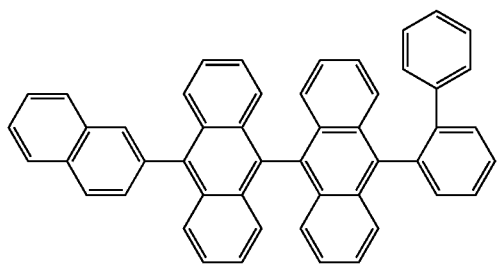
2a'-102
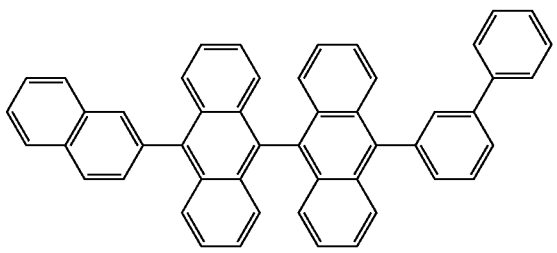
2a'-103
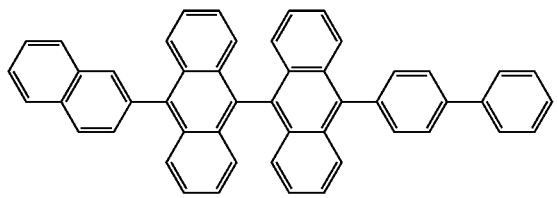
2a'-104
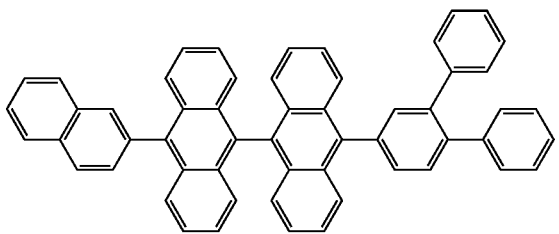
2a'-105
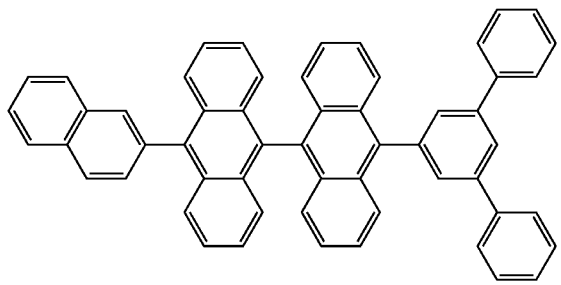
2a'-106
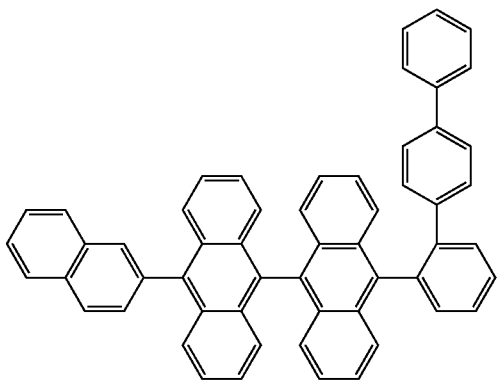

-continued
2a′-107
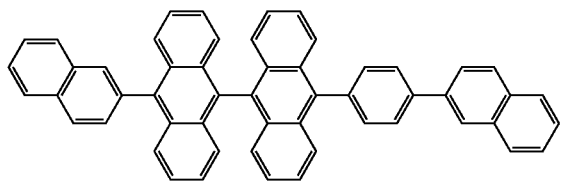
2a′-108
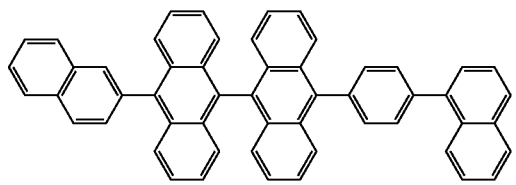
2a′-109
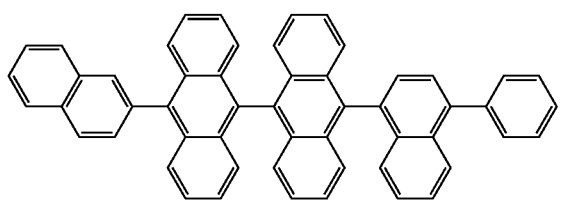
2a′-110
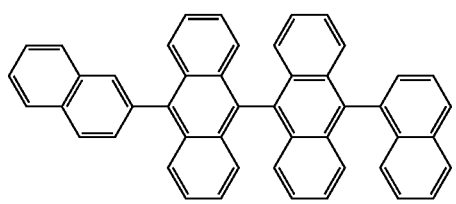
2a′-111
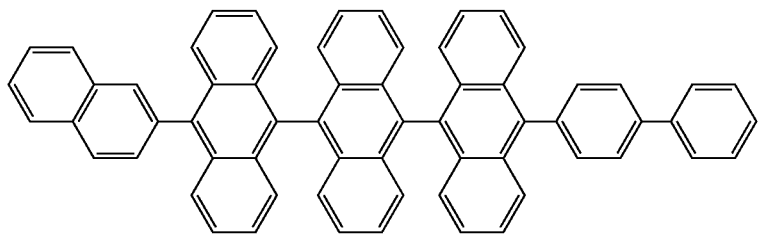
2a′-112
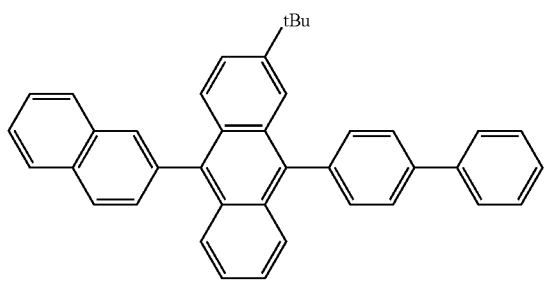
2a′-113
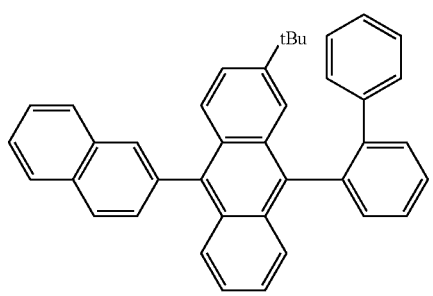
2a′-114
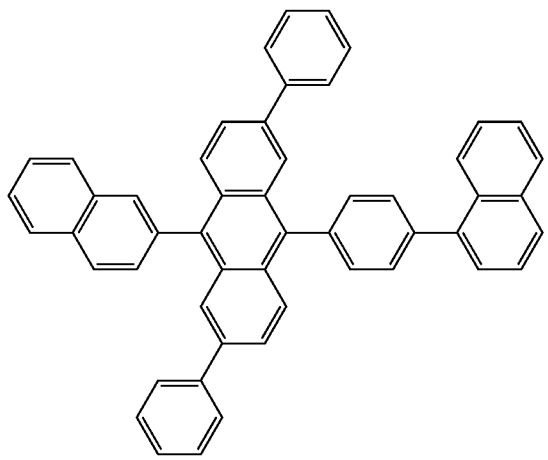

-continued
2aɛ-115
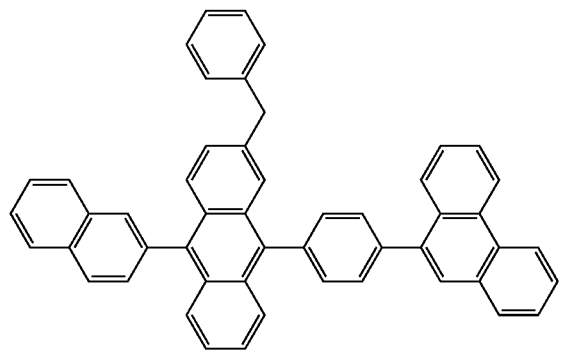
2aɛ-116
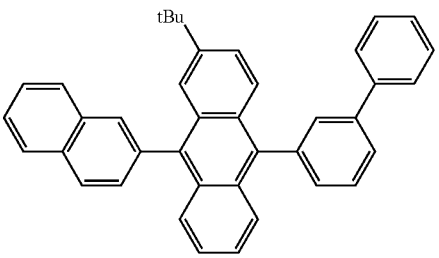
2a′-117
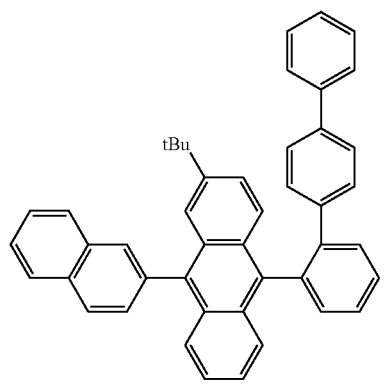
2a′-118
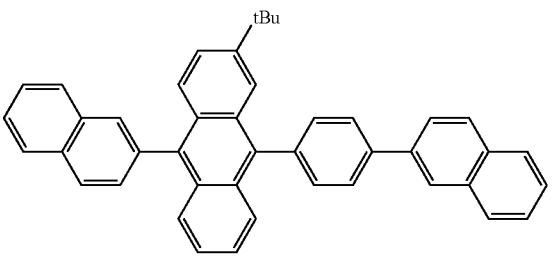
2a′-119
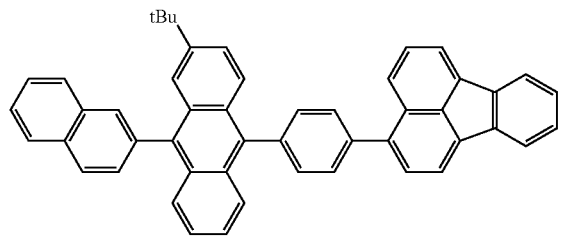
2a′-120
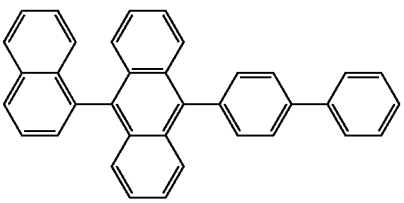
2a′-121
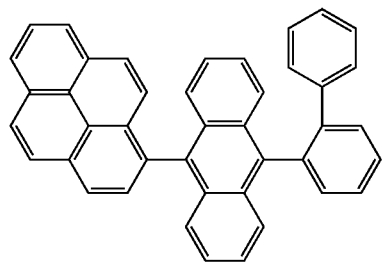
2a′-122
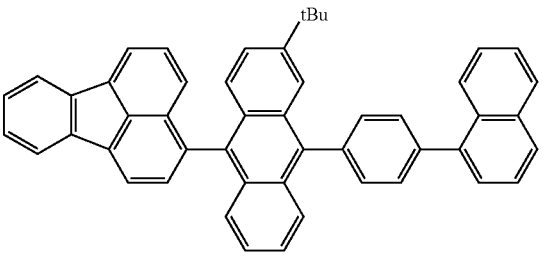
2a′-123
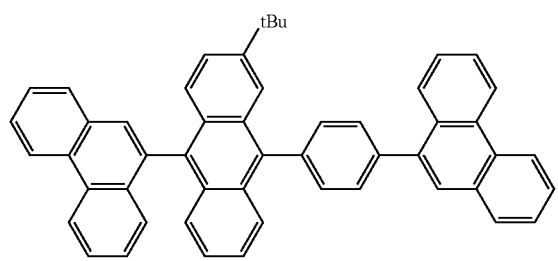
2a′-124
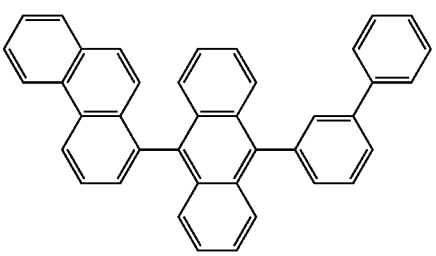

-continued
2a'-125
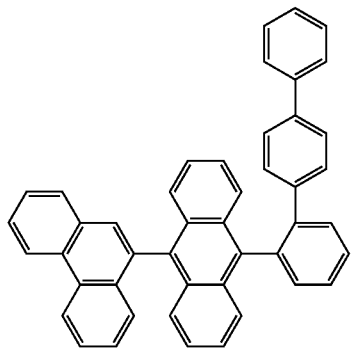
2a'-126
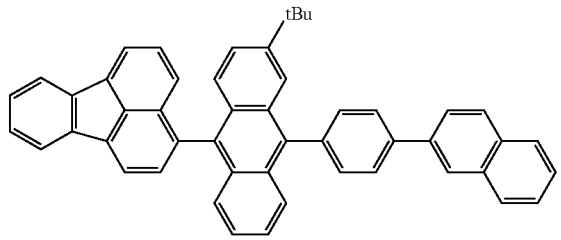
2a'-127
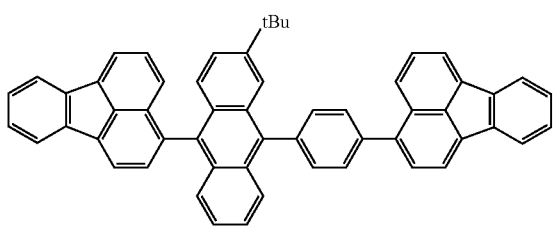
2a'-128
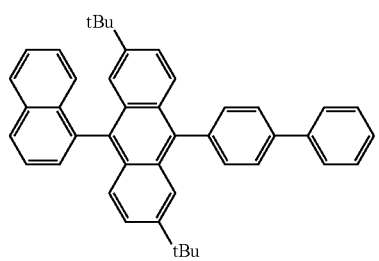
2a'-129
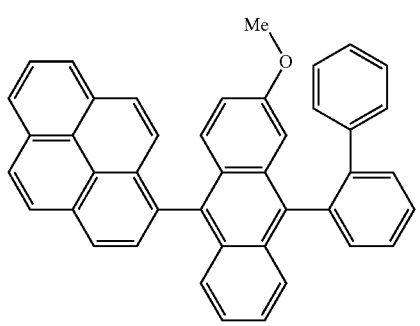
2a'-130
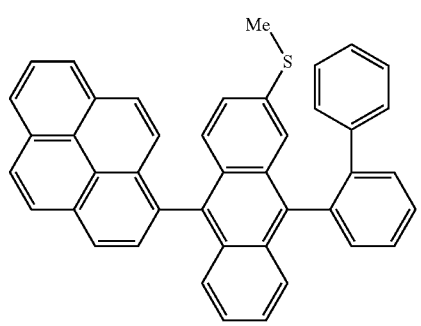
2a'-131
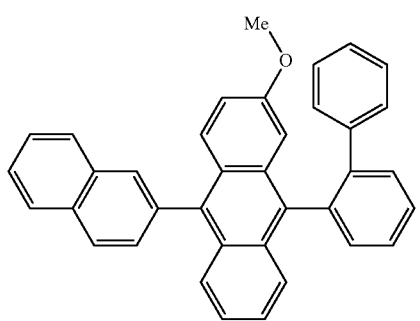
2a'-132
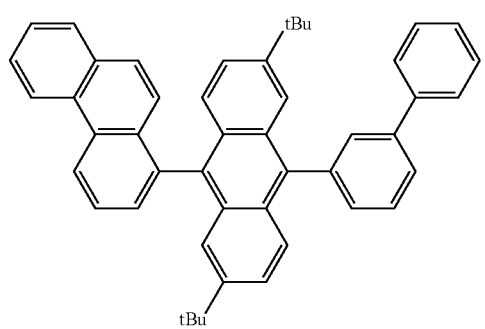

-continued
2a'-133
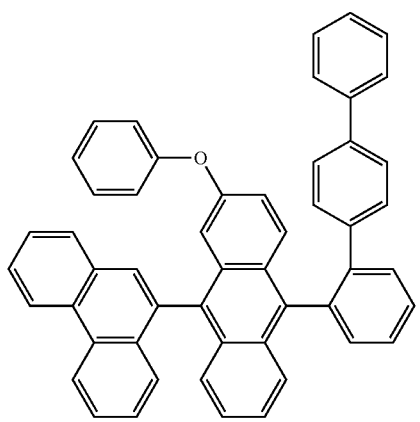
2a'-134
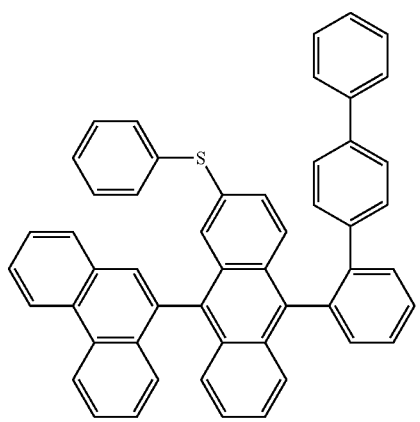
2a'-135
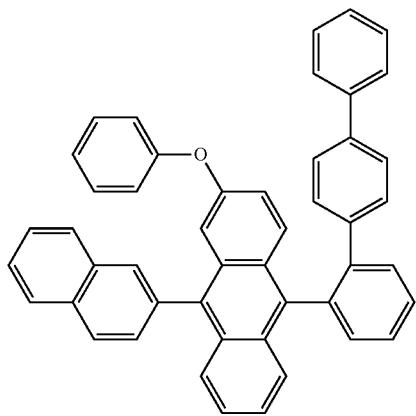
2a'-136
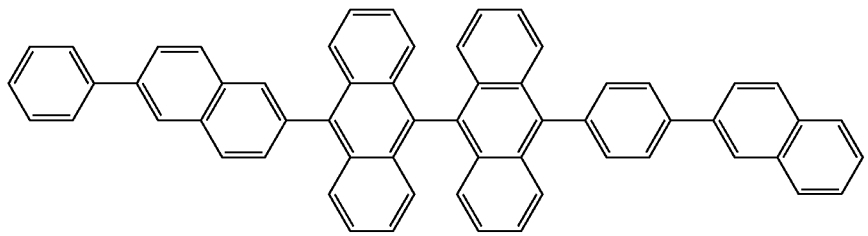
2a'-137
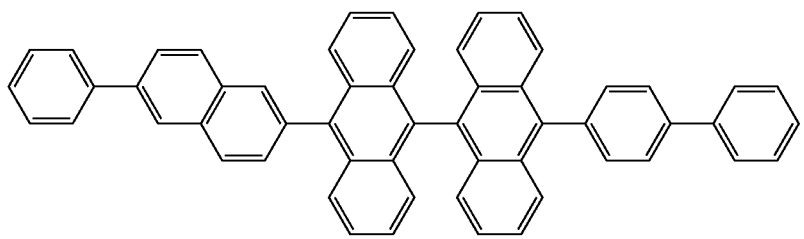
2a'-138
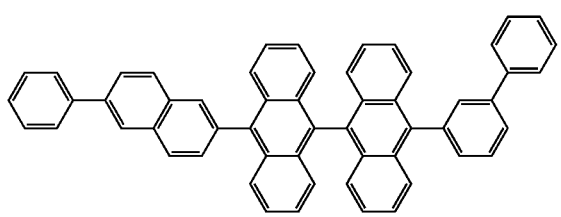
2a'-139
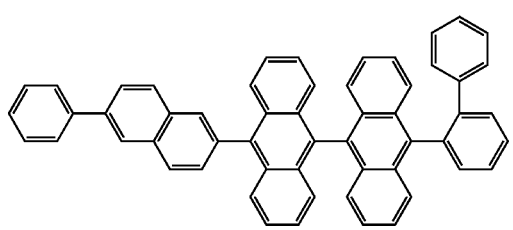

-continued
2a′-140
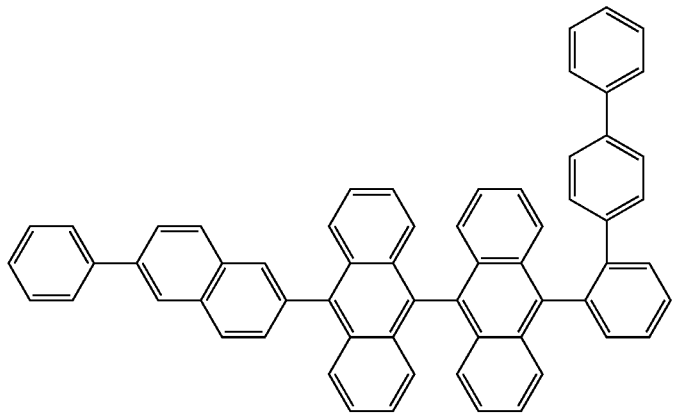
2a′-141
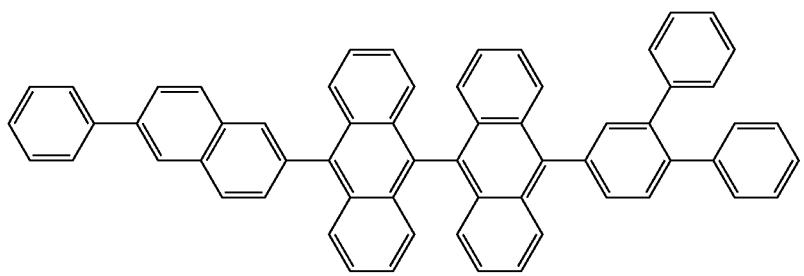
2a′-142
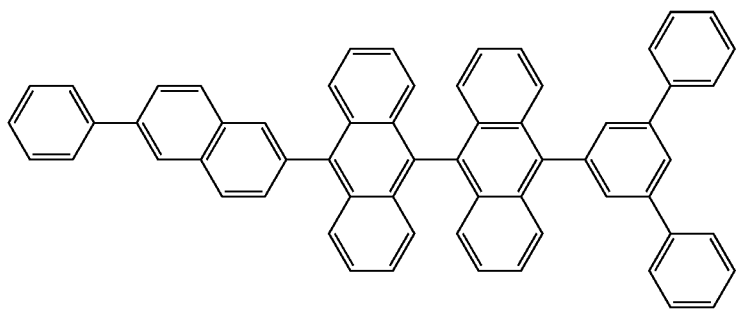
2a′-143
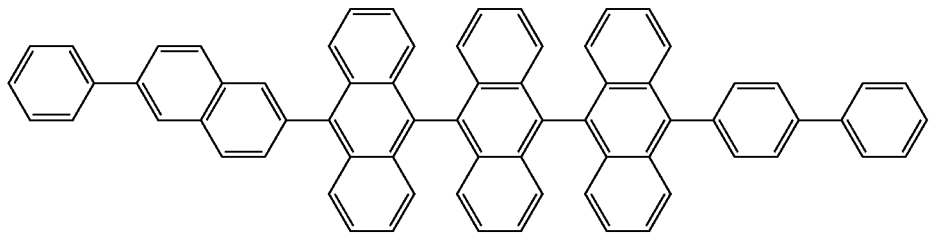
(ii)
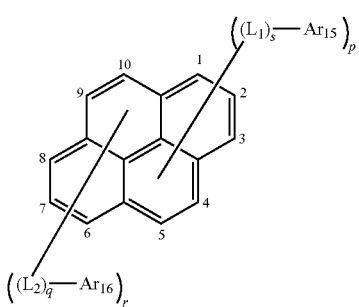
⟨?⟩ indicates text missing or illegible when filed (In the formula, $Ar_{15}$ and $Ar_{16}$ each independently represent a substituted or unsubstituted aryl group having 6 to 50 ring-forming carbon atoms;

$L_1$ and $L_2$ each independently represent a substituted or unsubstituted phenylene group, a substituted or unsubstituted naphthalenylene group, a substituted or unsubstituted fluorenylene group, or a substituted or unsubstituted dibenzosilolylene group;

s represents an integer of 0 to 2, p represents an integer of 1 to 4, q represents an integer of 0 to 2, and r represents an integer of 0 to 4; and $L_1$ or $Ar_{15}$ is bonded to any one of 1- to 5-positions of pyrene and $L_2$ or $Ar_{16}$ is bonded to any one of 6- to 10-positions of pyrene, provided that, when p+r is an even number, $Ar_{15}$, $Ar_{16}$, $L_1$, and $L_2$ satisfy the following condition (1) or (2):

(1) $Ar_{15} \neq Ar_{16}$ and/or $L_1 \neq L_2$ (where ≠ means that groups on both of its sides are different from each other in structure); or (2) when $Ar_{15}=Ar_{16}$ and $L_1=L_2$, (2-1) s≠q and/or p≠r, or (2-2) if s=q and p=r, (2-2-1) $L_1$ and $L_2$ are, or pyrene is, bonded to different bonding positions on $Ar_{15}$ and $Ar_{16}$, or (2-2-2) in the case where $L_1$ and $L_2$ are, or pyrene is, bonded to the same bonding positions on $Ar_{15}$ and $Ar_{16}$, substitution positions of $L_1$ and $L_2$ or $Ar_{15}$ and $Ar_{16}$ on pyrene exclude 1- and 6-positions or 2- and 7-positions.)

Specific examples of, and substituents for, the respective groups represented by $Ar_{15}$ and $Ar_{16}$, and $L_1$ and $L_2$ include the same examples as those described for the general formula (i).

Specific examples of the pyrene derivative represented by the general formula (ii) are shown below, however, the derivative is not limited to these exemplified compounds.

P1

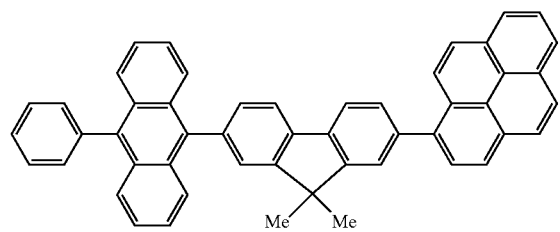

P2

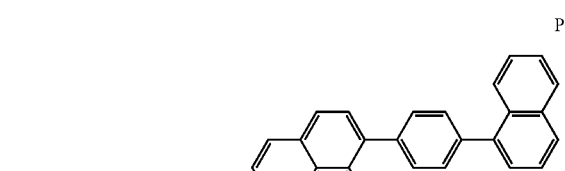

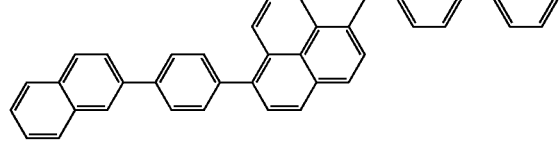

P3

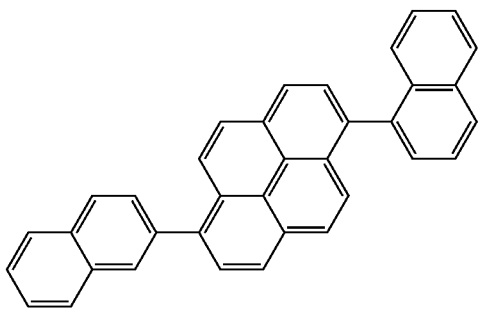

P4

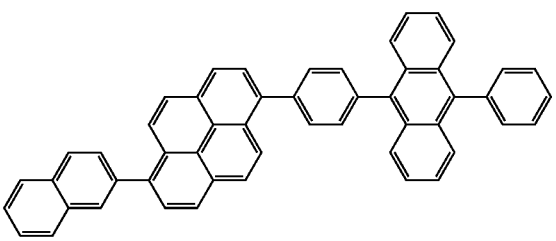

P5

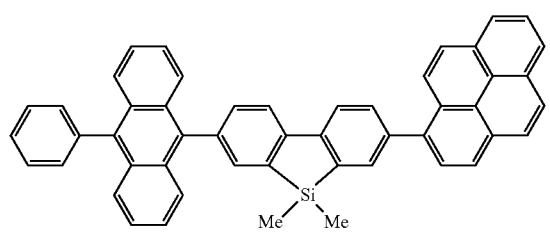

P6

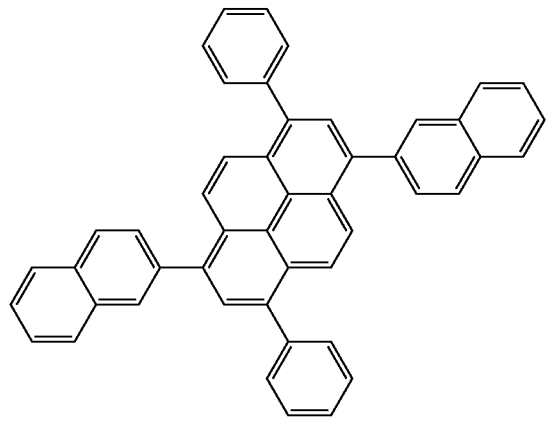

P7

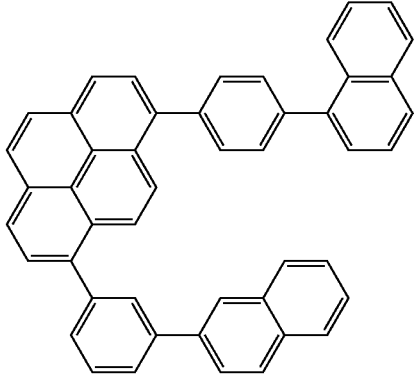

P8
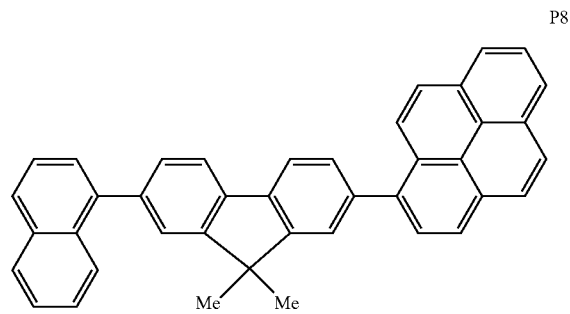
P9
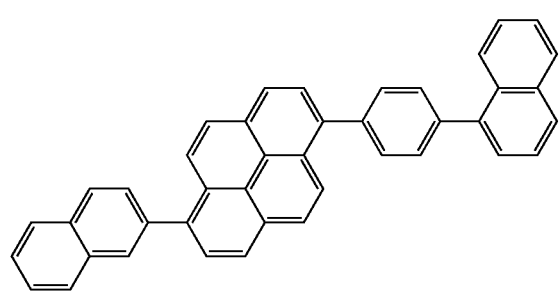
P10
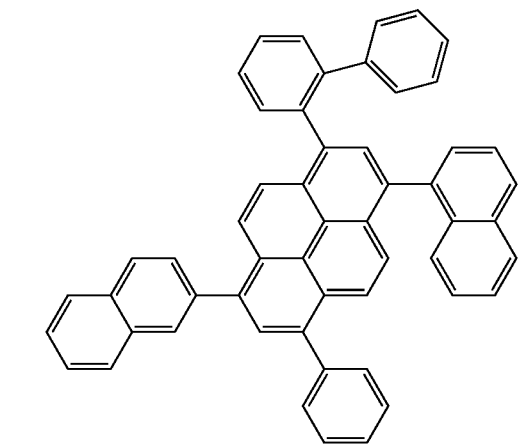
P12
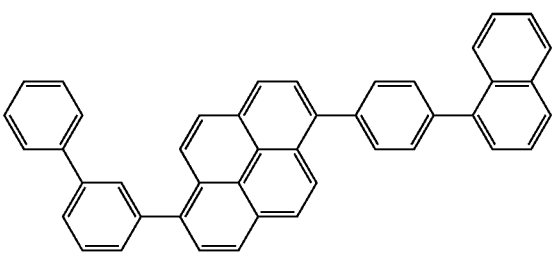
P13
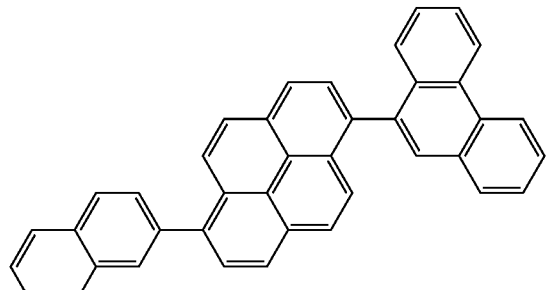
P14
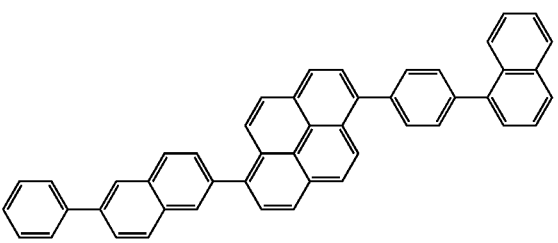
P15
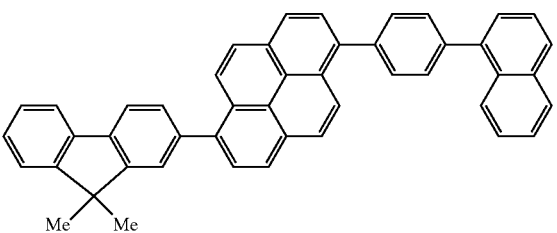
P16
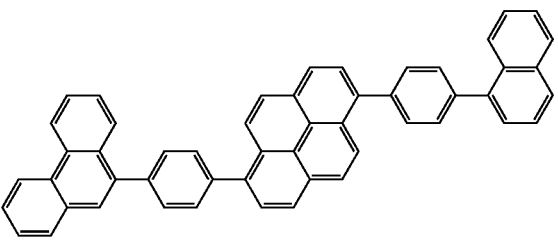
P17
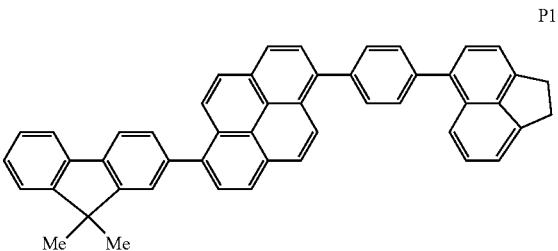
P11

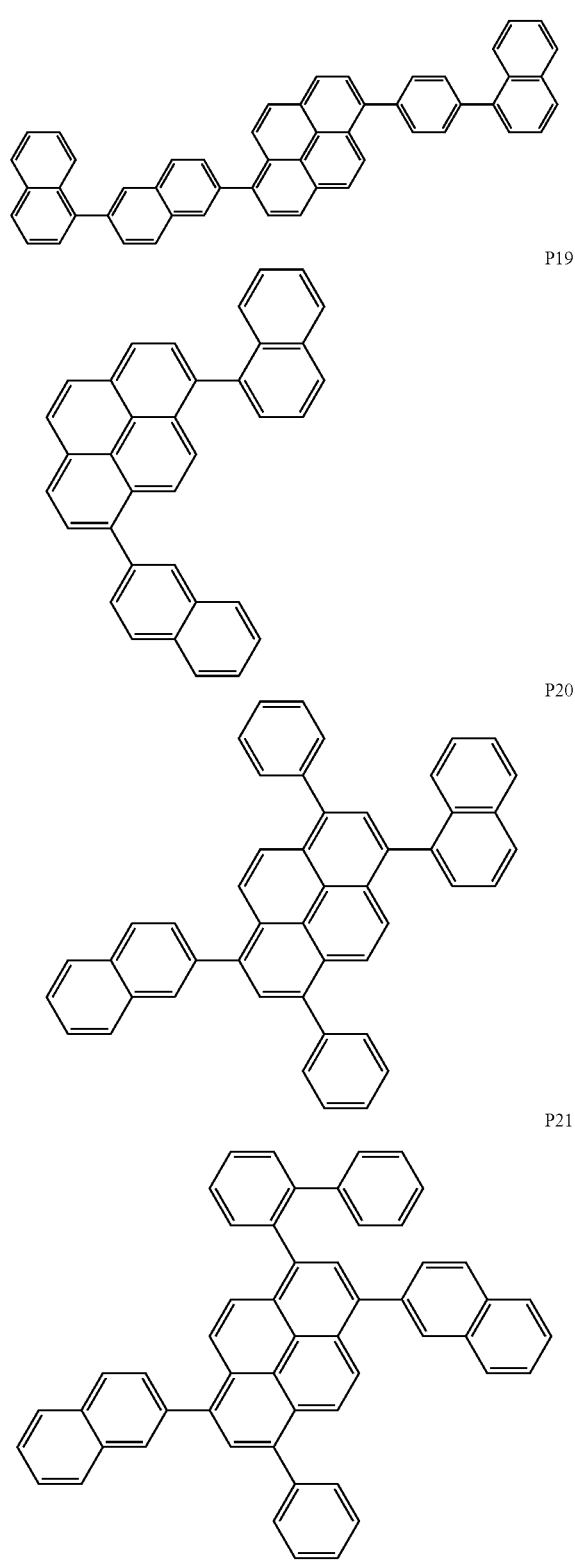

P18

P19

P20

P21

It should be noted that the number of carbon atoms or atoms of each group of each of the above-mentioned general formulae (i) to (ii) is a number excluding that of a substituent. In addition, the number of carbon atoms of an aralkyl group is the number of carbon atoms of an aryl portion.

An arbitrary substituent in the "substituted or unsubstituted . . . group" in each of the above-mentioned general formulae is, for example, a substituted or unsubstituted aryl group having 6 to 50 ring-forming carbon atoms, a substituted or unsubstituted alkyl group having 1 to 50 carbon atoms, a substituted or unsubstituted alkoxy group having 1 to 50 carbon atoms, a substituted or unsubstituted aralkyl group having 7 to 50 ring-forming carbon atoms, a substituted or unsubstituted aryloxy group having 6 to 50 ring-forming carbon atoms, a substituted or unsubstituted arylthio group having 6 to 50 ring-forming carbon atoms, a substituted or unsubstituted alkoxycarbonyl group having 1 to 50 carbon atoms, an amino group, a halogen atom, a cyano group, a nitro group, a hydroxyl group, or a carboxyl group.

In the present invention, the organic EL device having multiple organic thin film layers is a laminate having, for example, an (anode/hole injecting layer/light emitting layer/cathode), (anode/light emitting layer/electron injecting layer/cathode), or (anode/hole injecting layer/light emitting layer/electron injecting layer/cathode) structure.

If needed, in addition to the aromatic amine derivative of present invention, a known light emitting material, a doping material, a hole injecting material, or an electron injecting material may be further used in combination in the multiple layers. When the organic EL device has a structure of the multiple organic thin film layers, a reduction in luminance or lifetime due to quenching may be prevented. If needed, a light emitting material, a doping material, a hole injecting material, and an electron injecting material may be used in combination. Using a doping material in combination, improvements in emission luminance and luminous efficiency, and red or blue light emission may also be obtained. In addition, each of the hole injecting layer, the light emitting layer, and the electron injecting layer may be formed of a layer structure having two or more layers. At that time, in the case of the hole injecting layer, a layer for injecting a hole from the electrode is referred to as a hole injecting layer, and a layer for accepting the hole from the hole injecting layer and transporting the hole to the light emitting layer is referred to as a hole transporting layer. In the same manner, in the case of the electron injecting layer, a layer for injecting an electron from the electrode is referred to as an electron injecting layer, and a layer for accepting the electron from the electron injecting layer and transporting the electron to the light emitting layer is referred to as an electron transporting layer. Each of those layers is selected and used depending on factors such as the energy level of a material, heat resistance, and adhesiveness between the layer and an organic layer or a metal electrode.

Examples of a host material or a doping material other than those represented by the above-mentioned general formulae (i) and (ii) which may be used in the light emitting layer together with the aromatic amine derivative of the present invention include: polyfused aromatic compounds such as naphthalene, phenanthrene, rubrene, anthracene, tetracene, pyrene, perylene, chrysene, decacyclene, coronene, tetraphenylcyclopentadiene, pentaphenylcyclopentadiene, fluorene, spirofluorene, 9,10-diphenylanthracene, 9,10-bis(phenylethinyl)anthracene, and 1,4-bis(9'-ethinylanthracene)benzene and derivatives thereof; organic metal complexes such as tris(8-quinolinolato)aluminum and bis-(2-methyl-8-quinolinolato)-4-(phenylphenolato)aluminum; a triarylamine derivative; a styrylamine derivative; a stilbene derivative; a coumarin derivative; a pyrane derivative; an oxazone derivative; a benzothiazole derivative; a benzoxazole derivative; a benzimidazole derivative; a pyrazine derivative; a cinnamate derivative; a diketopyrrolopyrrole derivative; an acridone derivative; and a quinacridone derivative, but the material is not limited thereto.

A compound having an ability of transporting a hole, having a hole injection effect from an anode and an excellent hole injection effect to a light emitting layer or a light emitting material, having an ability of preventing the migration of an exciton generated in the light emitting layer to an electron injecting layer or an injecting material, and having excellent thin film-formability is preferred as a hole injecting material. Specific examples of the compound include, but are not limited to, a phthalocyanine derivative, a naphthalocyanine derivative, a porphyrin derivative, oxazole, oxadiazole, triazole, imidazole, imidazolone, imidazolethione, pyrazoline, pyrazolone, tetrahydroimidazole, oxazole, oxadiazole, hydrazone, acylhydrazone, polyarylalkane, stilbene, butadiene, benzidine type triphenylamine, styrylamine type triphenylamine, diamine type triphenylamine, derivatives thereof, and polymer materials such as polyvinyl carbazole, polysilane, and a conductive polymer.

Of the hole injecting materials that may be used in the organic EL device of the present invention, more effective hole injecting materials are an aromatic tertiary amine derivative and a phthalocyanine derivative.

Examples of the aromatic tertiary amine derivative include, but are not limited to, triphenylamine, tritolylamine, tolyldiphenylamine, N,N'-diphenyl-N,N'-(3-methylphenyl)-1,1'-biphenyl-4,4'-diamine, N,N,N',N'-(4-methylphenyl)-1,1'-phenyl-4,4'-diamine, N,N,N',N'-(4-methylphenyl)-1,1'-biphenyl-4,4'-diamine, N,N'-diphenyl-N,N'-dinaphthyl-1,1'-biphenyl-4,4'-diamine, N,N'-(methylphenyl)-N,N'-(4-n-butylphenyl)-phenanthrene-9,10-diamine, N,N-bis(4-di-4-tolylaminophenyl)-4-phenyl-cyclohexane, and an oligomer or a polymer having one of the aromatic tertiary amine skeletons.

Examples of the phthalocyanine (Pc) derivative include, but are not limited to, phthalocyanine derivatives such as H$_2$Pc, CuPc, CoPc, NiPc, ZnPc, PdPc, FePc, MnPc, ClAlPc, ClGaPc, ClInPc, ClSnPc, Cl$_2$SiPc, (HO)AlPc, (HO)GaPc, VOPc, TiOPc, MoOPc, and GaPc-O—GaPc, and naphthalocyanine derivatives.

In addition, the organic EL device of the present invention is preferably formed of a layer containing each of those aromatic tertiary amine derivatives and/or each of phthalocyanine derivatives, such as the hole transporting layer or the hole injecting layer, between a light emitting layer and an anode.

A compound having an ability of transporting electrons, having an electron injection effect from a cathode and an excellent electron injection effect to a light emitting layer or a light emitting material, having an ability of preventing the migration of an exciton generated in the light emitting layer to the hole injecting layer, and having excellent thin film-formability is preferred as an electron injecting material.

As specific examples of an electron injecting material, a metal complex of 8-hydroxyquinoline or of a derivative of 8-hydroxyquinoline, or an oxadiazole derivative is suitable. Specific examples of the metal complex of 8-hydroxyquinoline or of the derivative of 8-hydroxyquinoline that can be used as an electron injecting material include metal chelate oxynoid compounds each containing a chelate of oxine (generally 8-quinolinol or 8-hydroxyquinoline) such as tris(8-quinolinolato)aluminum.

On the other hand, examples of the oxadiazole derivative include electron transfer compounds represented by the following general formula:

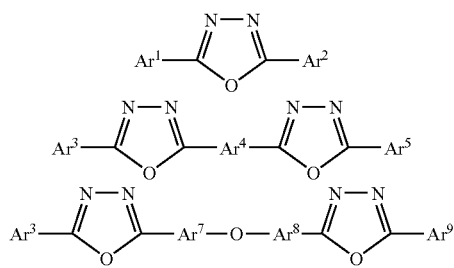

(in the formula, Ar$^1$, Ar$^2$, Ar$^3$, Ar$^5$, Ar$^6$, and Ar$^9$ each represent a substituted or unsubstituted aryl group and may be identical to or different from each other; and Ar$^4$, Ar$^7$ and Ar$^8$ each represent a substituted or unsubstituted arylene group and may be identical to or different from each other.)

Examples of the aryl group include a phenyl group, a biphenyl group, an anthranyl group, a perylenyl group, and a pyrenyl group. Examples of the arylene group include a phenylene group, a naphthylene group, a biphenylene group, anthranylene group, a perylenylene group, and a pyrenylene group. Examples of the substituent include alkyl groups each having 1 to 10 carbon atoms, alkoxy groups each having 1 to 10 carbon atoms, and a cyano group. As the electron transfer compound, compounds having a thin film forming property are preferred.

Specific examples of the electron transfer compounds described above include the following.

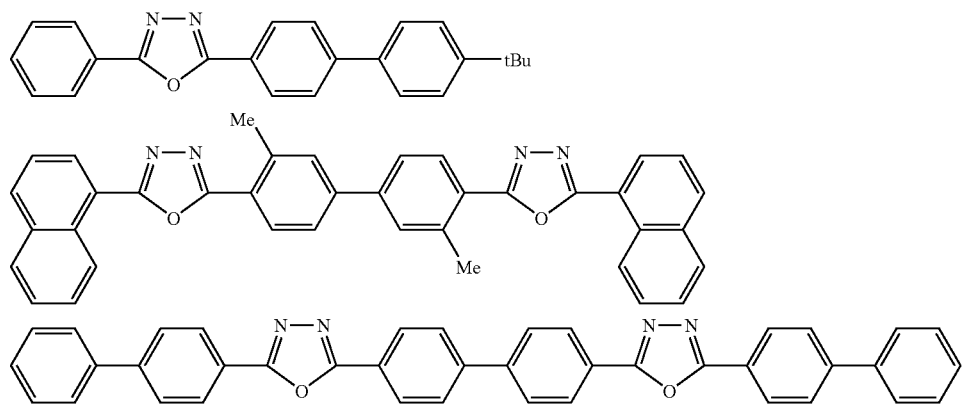

-continued

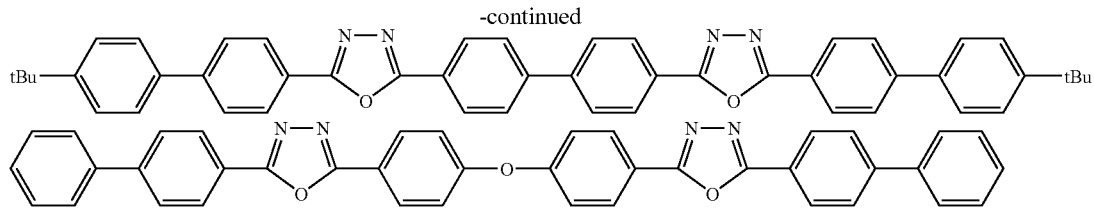

Further, materials represented by the following general formulae (A) to (F) can be used in the electron injecting material:

nitrogen-containing heterocyclic derivatives represented by the general formulae (A) and (B):

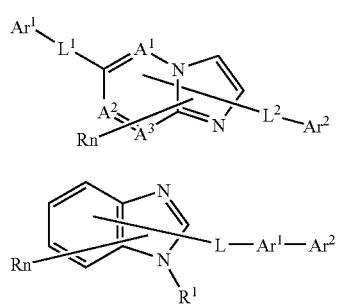

(in the general formulae (A) and (B): $A^1$ to $A^3$ each independently represent a nitrogen atom or a carbon atom, $Ar^1$ represents a substituted or unsubstituted aryl group having 6 to 60 ring-forming carbon atoms, or a substituted or unsubstituted heteroaryl group having 3 to 60 ring-forming atoms, $Ar^2$ represents a hydrogen atom, a substituted or unsubstituted aryl group having 6 to 60 ring-forming carbon atoms, a substituted or unsubstituted heteroaryl group having 3 to 60 ring-forming carbon atoms, a substituted or unsubstituted alkyl group having 1 to 20 carbon atoms, or a substituted or unsubstituted alkoxy group having 1 to 20 carbon atoms, or a divalent group of any one of those groups provided that one of $Ar^1$ and $Ar^2$ represents a substituted or unsubstituted fused ring group having 10 to 60 ring-forming carbon atoms or a substituted or unsubstituted monohetero fused ring group having 3 to 60 ring-forming atoms;

$L^1$, $L^2$, and L each independently represent a single bond, a substituted or unsubstituted arylene group having 6 to 60 ring-forming carbon atoms, a substituted or unsubstituted heteroarylene group having 3 to 60 ring-forming atoms, or a substituted or unsubstituted fluorenylene group;

R represents a hydrogen atom, a substituted or unsubstituted aryl group having 6 to 60 ring-forming carbon atoms, a substituted or unsubstituted heteroaryl group having 3 to 60 ring-forming atoms, a substituted or unsubstituted alkyl group having 1 to 20 carbon atoms, or a substituted or unsubstituted alkoxy group having 1 to 20 carbon atoms n represents an integer of 0 to 5, and, when n represents 2 or more, multiple R's may be identical to or different from each other, and multiple R groups adjacent to each other may be bonded to each other to form a carbocyclic aliphatic ring or a carbocyclic aromatic ring);

A nitrogen-containing heterocyclic ring derivative represented by the general formula (C):

$$HAr-L-Ar^1—Ar^2 \qquad (C)$$

(in the formula, HAr represents a nitrogen-containing heterocyclic ring which has 3 to 90 carbon atoms and may have a substituent, L represents a single bond, an arylene group which has 6 to 60 carbon atoms and may have a substituent, a heteroarylene group which has 3 to 60 carbon atoms and may have a substituent, or a fluorenylene group which may have a substituent, $Ar^1$ represents a divalent aromatic hydrocarbon group which has 6 to 60 carbon atoms and may have a substituent, and $Ar^2$ represents an aryl group which has 6 to 60 carbon atoms and may have a substituent, or a heteroaryl group which has 3 to 60 carbon atoms and may have a substituent);

a silacyclopentadiene derivative represented by the general formula (D):

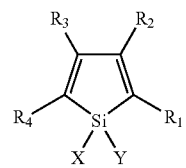

(in the formula, X and Y each independently represent a saturated or unsaturated hydrocarbon group having 1 to 6 carbon atoms, an alkoxy group, an alkenyloxy group, an alkynyloxy group, a hydroxyl group, a substituted or unsubstituted aryl group, or a substituted or unsubstituted heterocycle, or X and Y are bonded to each other to form a structure as a saturated or unsaturated ring; and $R_1$ to $R_4$ each independently represent hydrogen, a halogen atom, a substituted or unsubstituted alkyl group having 1 to 6 carbon atoms, an alkoxy group, an aryloxy group, a perfluoroalkyl group, a perfluoroalkoxy group, an amino group, an alkylcarbonyl group, an arylcarbonyl group, an alkoxycarbonyl group, an aryloxycarbonyl group, an azo group, an alkylcarbonyloxy group, an arylcarbonyloxy group, an alkoxycarbonyloxy group, an aryloxycarbonyloxy group, a sulfinyl group, a sulfonyl group, a sulfanyl group, a silyl group, a carbamoyl group, an aryl group, a heterocyclic group, an alkenyl group, an alkynyl group, a nitro group, a formyl group, a nitroso group, a formyloxy group, an isocyano group, a cyanate group, an isocyanate group, a thiocyanate group, an isothiocyanate group, or a cyano group, or, when two or more of $R_1$ to $R_4$ are adjacent to each other, they form a structure in which substituted or unsubstituted rings are condensed);

a borane derivative represented by the general formula (E):

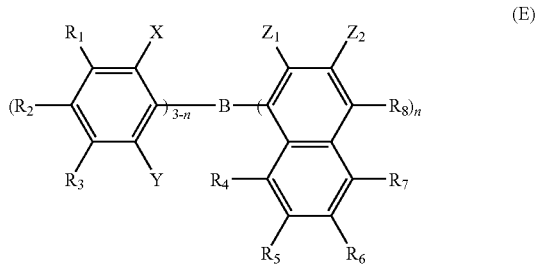

(E)

(in the formula, $R_1$ to $R_8$ and $Z_2$ each independently represent a hydrogen atom, a saturated or unsaturated hydrocarbon group, an aromatic hydrocarbon group, a heterocyclic group, a substituted amino group, a substituted boryl group, an alkoxy group, or an aryloxy group; X, Y, and $Z_1$ each independently represent a saturated or unsaturated hydrocarbon group, an aromatic hydrocarbon group, a heterocyclic group, a substituted amino group, an alkoxy group, or an aryloxy group; substituents of $Z_1$ and $Z_2$ may be bonded to each other to form a fused ring; and n represents an integer of 1 to 3, and, when n represents 2 or more, $Z_1$'s may be different from each other provided that the case where n represents 1, X, Y, and $R_2$ each represent a methyl group, $R_8$ represents a hydrogen atom or a substituted boryl group and the case where n represents 3 and $Z_1$'s each represent a methyl group are excluded);

(F)

(in the formula, $Q^1$ and $Q^2$ each independently represent a ligand represented by the following general formula (G); and L represents a halogen atom, a substituted or unsubstituted alkyl group, a substituted or unsubstituted cycloalkyl group, a substituted or unsubstituted aryl group, a substituted or unsubstituted heterocyclic group, —$OR^1$ (where $R^1$ represents a hydrogen atom, a substituted or unsubstituted alkyl group, a substituted or unsubstituted cycloalkyl group, a substituted or unsubstituted aryl group), or a substituted or unsubstituted heterocyclic group, or a ligand represented by —O—Ga-$Q^3(Q^4)$ (where $Q^3$ and $Q^4$ are identical to $Q^1$ and $Q^2$, respectively).)

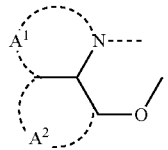

(G)

(In the formula, rings $A^1$ and $A^2$ are six-membered aryl ring structures which are condensed with each other and each of which may have a substituent.)

The metal complex behaves strongly as an n-type semiconductor, and has a large electron injecting ability. Further, generation energy upon formation of the complex is low. As a result, the metal and the ligand of the formed metal complex are bonded to each other so strongly that the fluorescent quantum efficiency of the complex as a light emitting material improves.

Specific examples of a substituent in the rings $A^1$ and $A^2$ which each form a ligand in the general formula (G) include: a halogen atom such as chlorine, bromine, iodine, or fluorine; a substituted or unsubstituted alkyl group such as a methyl group, an ethyl group, a propyl group, a butyl group, a s-butyl group, a t-butyl group, a pentyl group, a hexyl group, a heptyl group, an octyl group, a stearyl group, or trichloromethyl group; a substituted or unsubstituted aryl group such as a phenyl group, a naphthyl group, a 3-methylphenyl group, a 3-methoxyphenyl group, a 3-fluorophenyl group, a 3-trichloromethylphenyl group, a 3-trifluoromethylphenyl group, or a 3-nitrophenyl group; a substituted or unsubstituted alkoxy group such as a methoxy group, an n-butoxy group, a t-butoxy group, a trichloromethoxy group, a trifluoroethoxy group, a pentafluoropropoxy group, a 2,2,3,3-tetrafluoropropoxy group, a 1,1,1,3,3,3-hexafluoro-2-propoxy group, or a 6-(perfluoroethyl)hexyloxy group; a substituted or unsubstituted aryloxy group such as a phenoxy group, a p-nitrophenoxy group, p-t-butylphenoxy group, a 3-fluorophenoxy group, a pentafluorophenyl group, or a 3-trifluoromethylphenoxy group; a substituted or unsubstituted alkylthio group such as a methylthio group, an ethylthio group, a t-butylthio group, a hexylthio group, an octylthio group, or a trifluoromethylthio group; a substituted or unsubstituted arylthio group such as a phenylthio group, a p-nitrophenylthio group, a p-t-butylphenylthio group, a 3-fluorophenylthio group, a pentafluorophenylthio group, or a 3-trifluoromethylphenylthio group; a cyano group; a nitro group; an amino group; a mono-substituted or di-substituted amino group such as a methylamino group, a diethylamino group, an ethylamino group, a diethylamino group, a dipropylamino group, a dibutylamino group, or a diphenylamino group; an acylamino group such as a bis(acetoxymethyl)amino group, a bis(acetoxyethyl)amino group, a bis(acetoxypropyl)amino group, or a bis(acetoxybutyl)amino group; a hydroxyl group; a siloxy group; an acyl group; a carbamoyl group such as a methylcarbamoyl group, a dimethylcarbamoyl group, an ethylcarbamoyl group, a diethylcarbamoyl group, a propylcarbamoyl group, a butylcarbamoyl group, or a phenylcarbamoyl group; a carboxylic acid group; a sulfonic acid group; an imide group; a cycloalkyl group such as a cyclopentane group, or a cyclohexyl group; an aryl group such as a phenyl group, a naphthyl group, a biphenyl group, an anthranyl group, a phenanthryl group, a fluorenyl group, or a pyrenyl group; and a heterocyclic group such as a pyridinyl group, a pyrazinyl group, a pyrimidinyl group, a pyridazinyl group, a triazinyl group, an indolinyl group, a quinolinyl group, an acridinyl group, a pyrrolidinyl group, a dioxanyl group, a piperidinyl group, a morpholidinyl group, a piperazinyl group, a triathinyl group, a carbazolyl group, a furanyl group, a thiophenyl group, an oxazolyl group, an oxadiazolyl group, a benzoxazolyl group, a thiazolyl group, a thiadiazolyl group, a benzothiazolyl group, a triazolyl group, an imidazolyl group, a benzoimidazolyl group, or a puranyl group. In addition, the above-mentioned substituents may be bonded to each other to further form a six-membered aryl ring or a heterocycle.

A preferred embodiment of the organic EL device of the present invention includes a device including a reducing dopant in the region of electron transport or in the interfacial region of the cathode and the organic thin film layer. Here, the reducing dopant is defined as a substance which can reduce a compound having the electron-transporting property. Thus, various compounds can be used as the reducing dopant as long as the compounds have a certain reductive property. For example, at least one substance selected from the group consisting of alkali metals, alkaline earth metals, rare earth metals, alkali metal oxides, alkali metal halides, alkaline earth metal oxides, alkaline earth metal halides, rare earth metal oxides, rare earth metal halides, carbonates of alkali metals, carbonates of alkaline earth metals, organic complexes of alkali metals, organic complexes of alkaline earth metals, and organic complexes of rare earth metals can be suitably used.

In addition, more specifically, examples of the reducing dopant preferably include substances having a work function of 2.9 eV or less, examples of which include at least one alkali metal selected from the group consisting of Na (work function: 2.36 eV), K (work function: 2.28 eV), Rb (work function: 2.16 eV), and Cs (work function: 1.95 eV) and at least one alkaline earth metal selected from the group consisting of Ca (work function: 2.9 eV), Sr (work function: 2.0 to 2.5 eV), and Ba (work function: 2.52 eV). Of those, at least one alkali metal selected from the group consisting of K, Rb, and Cs is more preferred, Rb and Cs are still more preferred, and Cs is most preferred as the reducing dopant. Those alkali metals have high reducing ability, and the luminance of the emitted light and the life time of the organic EL device can be increased by addition of a relatively small amount of the alkali metal into the electron injecting zone. As the reducing dopant having a work function of 2.9 eV or less, combinations of two or more kinds of the alkali metals are also preferred. In particular, combinations having Cs such as the combinations of Cs and Na, Cs and K, Cs and Rb, and Cs, Na, and K are preferred. The reducing ability can be efficiently exhibited by the combination having Cs. The luminance of emitted light and the life time of the organic EL device can be increased by adding the combination having Cs into the electron injecting zone.

The present invention may further include an electron injecting layer which is composed of an insulating material or a semiconductor and disposed between the cathode and the organic layer. In this case, leak of electric current can be effectively prevented, and the electron injecting property can be improved. As the insulating material, at least one metal compound selected from the group consisting of alkali metal chalcogenides, alkaline earth metal chalcogenides, alkali metal halides, and alkaline earth metal halides is preferred. It is preferred that the electron injecting layer be composed of the alkali metal chalcogenide or the like because the electron injecting property can be further improved. Specifically, preferred examples of the alkali metal chalcogenide include $Li_2O$, $K_2O$, $Na_2S$, $Na_2Se$, and $Na_2O$. Preferred examples of the alkaline earth metal chalcogenide include CaO, BaO, SrO, BeO, BaS, and CaSe. In addition, preferred examples of the alkali metal halide include LiF, NaF, KF, CsF, LiCl, KCl, and NaCl. In addition, preferred examples of the alkaline earth metal halide include fluorides such as $CaF_2$, $BaF_2$, $SrF_2$, $MgF_2$, and $BeF_2$ and halides other than the fluorides.

In addition, examples of the semiconductor composing the electron injecting layer include oxides, nitrides, and oxide nitrides of at least one element selected from Ba, Ca, Sr, Yb, Al, Ga, In, Li, Na, Cd, Mg, Si, Ta, Sb, and Zn used alone or in combination of two or more. It is preferred that the inorganic compound composing the electron injecting layer form a crystallite or amorphous insulating thin film. When the electron injecting layer is composed of the insulating thin film described above, a more uniform thin film can be formed, and defects of pixels such as dark spots can be decreased. It should be noted that examples of the inorganic compound include alkali metal chalcogenides, alkaline earth metal chalcogenides, alkali metal halides, and alkaline earth metal halides which are described above.

Next, as the cathode, a material such as a metal, an alloy, a conductive compound, or a mixture of those materials which has a small work function (4 eV or less) is used. Specific examples of the electrode material include sodium, sodium-potassium alloys, magnesium, lithium, cesium, magnesium-silver alloys, aluminum/aluminum oxide, $Al/Li_2O$, Al/LiO, Al/Lif, aluminum-lithium alloys, indium, and rare earth metals.

The cathode can be prepared by forming a thin film of the electrode material by a process such as vapor deposition and sputtering.

Here, when the light emitted from the light emitting layer is obtained through the cathode, it is preferred that the cathode have a transmittance of the emitted light of more than 10%. It is also preferred that the sheet resistivity of the cathode be several hundred $\Omega/\square$ or less. Further, the thickness of the cathode is, in general, in the range of 10 nm to 1 μm and preferably in the range of 50 to 200 nm.

Further, defects in pixels generally tend to be formed in organic EL device due to leak and short circuit because an electric field is applied to ultra-thin films. To prevent the formation of the defects, a layer of a thin film having an insulating property may be inserted between the pair of electrodes.

Examples of the material used for the insulating layer include aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide, and vanadium oxide. Mixtures and laminates of the materials may also be used.

In the organic EL device of the present invention, in addition to at least one kind of aromatic amine derivative selected from the general formula (1), at least one kind of light emitting material, doping material, hole injecting material, and electron injecting material may be incorporated into the light emitting layers. In addition, the surface of the organic EL device obtained according to the present invention may be provided with a protective layer, or the entire device may be protected with silicone oil, a resin, or the like with a view to improving the stability of the device against temperature, humidity, an atmosphere, or the like.

A conductive material having a work function of more than 4 eV is suitably used in the anode of the organic EL device of the present invention. Examples of the conductive material to be used include: carbon, aluminum, vanadium, iron, cobalt, nickel, tungsten, silver, gold, platinum, palladium, and alloys thereof; metal oxides such as tin oxide and indium oxide to be used in an ITO substrate and an NESA substrate; and further, organic conductive resins such as polythiophene and polypyrrole. A conductive substance having a work function of less than 4 eV is suitably used in the cathode. Examples of the conductive substance to be used include, but are not limited to, magnesium, calcium, tin, lead, titanium, yttrium, lithium, ruthenium, manganese, aluminum, lithium fluoride, and alloys thereof. Representative examples of the alloys include, but are not limited to, a magnesium/silver alloy, a magnesium/indium alloy, and a lithium/aluminum alloy. A ratio between the components of the alloy is controlled depending on, for example, the temperature of a deposition source, an atmosphere, and the degree of vacuum, and is selected appropriately. Each of the anode and the cathode may be formed in a layer structure having two or more layers if needed.

It is desirable that at least one surface of the organic EL device of the present invention be sufficiently transparent in the emission wavelength region of the device so that the device may efficiently emit light. A substrate is also desirably transparent. A transparent electrode is formed by using any one of the above-mentioned conductive materials, and is set by a method such as deposition or sputtering in such a manner that desired translucency is secured. The light transmittance of an electrode on a light emitting surface is desirably or more. The substrate is not limited as long as it has mechanical strength, thermal strength, and transparency. Examples of the substrate include a glass substrate and a transparent resin film. Examples of the transparent resin film include polyethylene, an ethylene-vinyl acetate copolymer, an ethylene-vinyl alcohol copolymer, polypropylene, polystyrene, polymethyl methacrylate, polyvinyl chloride, polyvinyl alcohol, polyvinyl butyral, nylon, polyether ether ketone, polysulfone, polyether sulfone, a tetrafluoroethylene-perfluoroalkyl vinyl ether copolymer, polyvinyl fluoride, a tetrafluoroethylene-ethylene copolymer, a tetrafluoroethylene-hexafluoropropylene copolymer, polychlorotrifluoroethylene, polyvinylidene fluoride, polyester, polycarbonate, polyurethane, polyimide, polyether imide, polyimide, and polypropylene.

Any one of dry film forming methods such as vacuum deposition, sputtering, plasma, and ion plating, and wet film forming methods such as spin coating, dipping, and flow coating is applicable to the formation of each layer of the organic EL device according to the present invention. The thickness of each layer is not particularly limited, but must be set to an appropriate thickness. An excessively large thickness requires an increased applied voltage for obtaining certain optical output, resulting in poor efficiency. An excessively small thickness causes a pin hole or the like, with the result that sufficient emission luminance cannot be obtained even when an electric field is applied. In general, the thickness is in the range of preferably 5 nm to 10 µm, or more preferably 10 nm to 0.2 µm.

In the case of a wet film forming method, a material of which each layer is formed is dissolved or dispersed into an appropriate solvent such as ethanol, chloroform, tetrahydrofuran, or dioxane, to thereby form a thin film. At that time, any one of the solvents may be used. In addition, an appropriate resin or additive may be used in each of the organic thin film layers for, for example, improving film formability or preventing a pin hole in the film. Examples of an available resin include: insulating resins such as polystyrene, polycarbonate, polyallylate, polyester, polyamide, polyurethane, polysulfone, polymethyl methacrylate, polymethyl acrylate, and cellulose, and copolymers thereof; photoconductive resins such as poly-N-vinylcarbazole and polysilane; and conductive resins such as polythiophene and polypyrrole. In addition, examples of the additive include an antioxidant, a UV absorber, and a plasticizer.

The organic EL device of the present invention may find use in applications including a flat luminous body such as the flat panel display of a wall hanging television, a light source for the backlight, meters, or the like of a copying machine, a printer, or a liquid crystal display, a display panel, and a signal lamp. In addition, the material of the present invention may be used in not only the field of an organic EL device but also the fields of an electrophotographic photosensitive member, a photoelectric conversion device, a solar cell, an image sensor, and the like.

EXAMPLES

Next, the present invention is described in more detail by way of examples.

Synthesis Example 1

Synthesis of Compound D1

(1) Synthesis of N-(2-dibenzofuranyl)acetamide

In a stream of argon, 4.25 g of acetamide, 17.8 g of 2-bromodibenzofuran, 0.7 g of copper iodide, 0.63 g of N,N'-dimethylethylenediamine, 39.7 g of potassium carbonate, and xylene were subjected to a reaction under reflux for 12 hours.

After having been cooled, the resultant was filtrated, and then clean water and toluene were added to the filtrate so that an organic layer might be separated. The organic layer was washed with clean water three times, and was then concentrated under reduced pressure. As a result, 14.4 g of a yellowish white solid were obtained. The solid was identified as N-(2-dibenzofuranyl)acetamide by field desorption mass spectrometry (FD-MS).

(2) Synthesis of N-(2-dibenzofuranyl)-N-phenylacetamide

Synthesis was performed in the same manner as in the synthesis of N-(2-dibenzofuranyl)acetamide in the section (1) except that N-(2-dibenzofuranyl)acetamide was used instead of acetamide, and bromobenzene was used instead of 2-bromodibenzofuran. The resultant was identified as N-(2-dibenzofuranyl)-N-phenylacetamide by field desorption mass spectrometry (FD-MS).

(3) Synthesis of N-(2-dibenzofuranyl)-N-phenylamine

First, 7.9 g of N-(2-dibenzofuranyl)-N-phenylacetamide, 8.8 g of potassium hydroxide, 10 mL of clean water, 25 mL of ethanol, and 50 mL of toluene were loaded, and then the mixture was subjected to a reaction under reflux for 7 hours.

After the resultant had been cooled, clean water was added to the resultant, and then the mixture was filtrated. Clean water and toluene were added to the filtrate so that an organic layer might be separated. The organic layer was washed with clean water three times, and was then concentrated. The resultant coarse product was recrystallized with toluene and ethanol, and then the resultant solid was dried under reduced pressure. As a result, 4.2 g of a white solid were obtained. The solid was identified as N-(2-dibenzofuranyl)-N-phenylamine by FD-MS.

(4) Synthesis of Compound D1

In a stream of argon, 4.2 g of N-(2-dibenzofuranyl)-N-phenylamine, 2.8 g of 6,12-dibromochrysene, 186 mg of $Pd_2(dba)_3$, 259 mg of $P(t-Bu)_3$, 4.3 g of t-butoxysodium, and 20 mL of toluene were loaded, and then the mixture was subjected to a reaction at 80° C. for 4 hours.

After the resultant had been cooled, toluene was added to the resultant, and then the mixture was subjected to celite filtration. After that, the filtrate was concentrated, and then the resultant concentrate was purified by silica gel chromatography (hexane:dichloromethane=6:1). The resultant solid was washed with n-hexane, and was then dried under reduced pressure. As a result, 3.2 g of a yellowish white solid were obtained. The solid was identified as Compound D1 by FD-MS.

Synthesis Example 2

Synthesis of Compound D21

Synthesis was performed in the same manner as in the foregoing except that 9,10-dibromoanthracene was used instead of 6,12-dibromochrysene in the section (4) of Synthesis Example 1. The resultant was identified as Compound D21 by FD-MS.

Synthesis Example 3

Synthesis of Compound D57

(1) Synthesis of N,N-(di-2-dibenzofuranyl)acetamide

In a stream of argon, 4.25 g of acetamide, 37.0 g of 2-bromodibenzofuran, 0.7 g of copper iodide, 0.63 g of N,N'-dimethylethylenediamine, 39.7 g of potassium carbonate, and xylene were subjected to a reaction under reflux for 12 hours.
After having been cooled, the resultant was filtrated, and then clean water and toluene were added to the filtrate so that an organic layer might be separated. The organic layer was washed with clean water three times, and was then concentrated under reduced pressure. As a result, 22.5 g of a white solid were obtained. The solid was identified as N,N-(di-2-dibenzofuranyl)acetamide by FD-MS.

(2) Synthesis of N,N-(di-2-dibenzofuranyl)amine

Synthesis was performed in the same manner as in the section (3) of Synthesis Example 1 except that N,N-(di-2-dibenzofuranyl)acetamide synthesized in the section (1) was used instead of N-(2-dibenzofuranyl)-N-phenylacetamide in the synthesis of N-(2-dibenzofuranyl)-N-phenylamine. The resultant was identified as N,N-(di-2-dibenzofuranyl)amine by FD-MS.

(3) Synthesis of Compound D57

Synthesis was performed in the same manner as in the section (4) of Synthesis Example 1 except that 1,5-di-t-butyl-3,7-dibromonaphthalene was used instead of 6,12-dibromochrysene, and N,N-(di-2-dibenzofuranyl)amine was used instead of N-(2-dibenzofuranyl)-N-phenylamine. The resultant was identified as Compound D57 by FD-MS.

Example 1

A transparent electrode formed of indium tin oxide and having a thickness of 120 nm was provided on a glass substrate measuring 25 mm by 75 mm by 1.1 mm. The glass substrate was subjected to UV/ozone irradiation, and washed. After that, the substrate was placed in a vacuum deposition apparatus.
First, N',N"-bis[4-(diphenylamino)phenyl]-N',N"-diphenylbiphenyl-4,4'-diamine was deposited from the vapor so as to serve as a hole injecting layer having a thickness of 60 nm. After that, N,N,N',N'-tetrakis(4-biphenyl)-4,4'-benzidine was deposited from the vapor onto the layer so as to serve as a hole transporting layer having a thickness of 20 nm. Next, 10,10'-bis[1,1',4',1"]terphenyl-2-yl-9,9'-bianthracenyl (BT-BAN) as a host material and Compound D1 described above as a doping material were simultaneously deposited from the vapor at a weight ratio of 40:2 so that a light emitting layer having a thickness of 40 nm might be formed.
Next, tris(8-hydroxyquinolinato)aluminum was deposited from the vapor onto the light emitting layer so as to serve as an electron injecting layer having a thickness of 20 nm. Then, lithium fluoride was deposited from the vapor so as to have a thickness of 1 nm, and then aluminum was deposited from the vapor so as to have a thickness of 150 nm. The aluminum/lithium fluoride functions as a cathode. Thus, an organic EL device was produced.
The resultant device was then subjected to an energization test. As a result, blue light emission having a current efficiency of 6.1 cd/A and an emission luminance of 600 cd/m$^2$ (luminous maximum wavelength: 458 nm) was obtained at a voltage of 6.4 V and a current density of 10 mA/cm$^2$. A continuous DC energization test was performed at an initial luminance of 500 cd/m$^2$. As a result, a half lifetime was 10,000 hours.

Example 2

An organic EL device was produced in the same manner as in Example 1 except that Compound D50 was used instead of Compound D1 as a doping material.
The resultant device was subjected to an energization test. As a result, green light emission having a current efficiency of 18.1 cd/A and an emission luminance of 1800 cd/m$^2$ (luminous maximum wavelength: 520 nm) was obtained at a voltage of 6.0 V end a current density of 10 mA/cm$^2$. A continuous DC energization test was performed at an initial luminance of 500 cd/m$^2$. As a result, a half lifetime was 35,000 hours.

Example 3

An organic EL device was produced in the same manner as in Example 1 except that Compound D22 was used instead of Compound D1 as a doping material.
The resultant device was subjected to an energization test. As a result, blue light emission having a current efficiency of 7.5 cd/A and an emission luminance of 750 cd/m$^2$ (luminous maximum wavelength: 466 nm) was obtained at a voltage of 6.2 V and a current density of 10 mA/cm$^2$. A continuous DC energization test was performed at an initial luminance of 500 cd/m$^2$. As a result, a half lifetime was 14,000 hours.

Comparative Example 1

An organic EL device was produced in the same manner as in Example 1 except that 6,12-bis(diphenylamino)chrysene was used instead of Compound D1 as a doping material.
The resultant device was subjected to an energization test. As a result, blue light emission having a current efficiency of 3.5 cd/A and an emission luminance of 311 cd/m$^2$ (luminous maximum wavelength: 451 nm) was obtained at a voltage of 6.2 V and a current density of 10 mA/cm$^2$. A continuous DC energization test was performed at an initial luminance of 500 cd/m$^2$. As a result, a half lifetime was as short as 1000 hours.

INDUSTRIAL APPLICABILITY

As specifically described above, the organic EL device using the aromatic amine derivative of the present invention has high luminous efficiency, hardly deteriorates even after long-term use, and has a long lifetime. Therefore, the organic EL device is useful as a flat luminous body of a wall hanging television or a light source for backlight or the like of a display.

The invention claimed is:

1. An aromatic amine derivative represented by the following general formula (1):

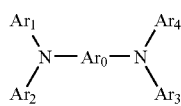

where $Ar_0$ represents a substituted or unsubstituted naphthylene group, a substituted or unsubstituted anthracenylene group, a substituted or unsubstituted phenanthrylene group, a substituted or unsubstituted chrysenylene group, a substituted or unsubstituted pyrenylene group, a substituted or unsubstituted benzoanthracenylene group, a substituted or unsubstituted fluoranthenylene group, a substituted or unsubstituted benzofluoranthenylene group, a substituted or unsubstituted perylenylene group, a substituted or unsubstituted coronenylene group, a substituted or unsubstituted picenylene group, a substituted or unsubstituted diphenylanthracenylene group, a substituted or unsubstituted triphenylylene group, a substituted or unsubstituted rubicenylene group, a substituted or unsubstituted phenylanthracenylene group, a substituted or unsubstituted bisanthracenylene group, a substituted or unsubstituted dianthracenylbenzynylene group, and a substituted or unsubstituted dibenzoanthracenylene group, and $Ar_1$ to $Ar_4$ each independently represent a substituted or unsubstituted aryl group having 6 to 50 ring-forming carbon atoms, a substituted or unsubstituted alkyl group having 1 to 50 carbon atoms, a substituted or unsubstituted cycloalkyl group having 3 to 50 ring-forming carbon atoms, a substituted or unsubstituted aralkyl group having 7 to 50 ring-forming carbon atoms, or a substituted or unsubstituted heterocyclic group having 5 to 50 ring-forming atoms, provided that one or more of $Ar_1$ to $Ar_4$ each represent a group represented by the following general formula (3):

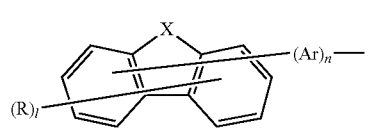

where n represents an integer of 0 to 3, l represents an integer of 0 to 7, X represents oxygen (O), sulfur (S), or selenium (Se), Ar represents a substituted or unsubstituted arylene group having 6 to 60 ring-forming carbon atoms, R represents a substituted or unsubstituted aryl group having 6 to 60 ring-forming carbon atoms, a substituted or unsubstituted alkyl group having 1 to 50 carbon atoms, an amino group, a substituted or unsubstituted alkoxy group having 1 to 50 carbon atoms, a substituted or unsubstituted aryloxy group having 6 to 50 ring-forming carbon atoms, a substituted or unsubstituted arylthio group having 6 to 50 ring-forming atoms, a substituted or unsubstituted alkoxycarbonyl group having 1 to 50 carbon atoms, a halogen atom, a cyano group, a nitro group, a hydroxyl group, a silyl group, or a carboxyl group, when n or l represents 2 or more, multiple Ar's or multiple R's may be identical to or different from each other, and when multiple R's are present, the multiple R's may be bonded to each other to form a saturated or unsaturated, five- or six-membered cyclic structure that may be substituted, provided that:
in the general formula (3), a case where $(R)_l$ and $(Ar)_n$ are bonded to a five-membered ring portion including X is excluded.

2. The aromatic amine derivative according to claim 1, wherein $Ar_0$ in the general formula (1) represents a substituted or unsubstituted naphthylene group, a substituted or unsubstituted anthracenylene group, a substituted or unsubstituted phenanthrylene group, a substituted or unsubstituted chrysenylene group, a substituted or unsubstituted pyrenylene group, or a substituted or unsubstituted benzoanthracenylene group.

3. The aromatic amine derivative according to claim 2, wherein —$NAr_1Ar_2$ and —$NAr_3Ar_4$ are bonded to 2- and 6-positions of the naphthylene group, respectively, —$NAr_1Ar_2$ and —$NAr_3Ar_4$ are bonded to 9- and 10-positions of the anthracenylene group, respectively, —$NAr_1Ar_2$ and —$NAr_3Ar_4$ are bonded to 2- and 6-positions of the anthracenylene group, respectively, —$NAr_1Ar_2$ and —$NAr_3Ar_4$ are bonded to 2- and 7-positions of the phenanthrylene group, respectively, —$NAr_1Ar_2$ and —$NAr_3Ar_4$ are bonded to 6- and 12-positions of the chrysenylene group, respectively, —$NAr_1Ar_2$ and —$NAr_3Ar_4$ are bonded to 1- and 6-positions of the pyrenylene group, respectively, —$NAr_1Ar_2$ and —$NAr_3Ar_4$ are bonded to 2- and 7-positions of the pyrenylene group, respectively, or —$NAr_1Ar_2$ and —$NAr_3Ar_4$ are bonded to 7- and 12-positions of the benzoanthracenylene group, respectively.

4. The aromatic amine derivative according to claim 1, wherein $Ar_1$ and $Ar_3$ in the general formula (1) each represent a group represented by the general formula (3).

5. The aromatic amine derivative according to claim 1, wherein all of $Ar_1$ to $Ar_4$ in the general formula (1) represent a group represented by the general formula (3).

6. The aromatic amine derivative according to claim 1, wherein n in the general formula (3) represents 0.

7. The aromatic amine derivative according to claim 1, wherein l in the general formula (3) represent 0.

8. The aromatic amine derivative according to claim 1, wherein X in the general formula (3) represents an oxygen atom.

9. The aromatic amine derivative according to claim 1, wherein, when n in the general formula (3) represents 0, X represents an oxygen atom, and a bonding position is present at a 2-position of a fused ring including X.

10. The aromatic amine derivative according to claim 1, wherein X in the general formula (3) represents a sulfur atom.

11. The aromatic amine derivative according to claim 1, wherein, when n in the general formula (3) represents 0, X represents a sulfur atom, and a bonding position is present at a 2-position of a fused ring including X.

12. The aromatic amine derivative according to claim 1, wherein R in the general formula (3) represents a silyl group.

13. An organic electroluminescence device comprising a light emitting material, which is the aromatic amine derivative according to claim 1.

14. An organic electroluminescence device comprising a blue light emitting material, which is the aromatic amine derivative according to claim 1.

15. An organic electroluminescence device comprising a green light emitting material, which is the aromatic amine derivative according to claim 1.

16. An organic electroluminescence device comprising a doping material, which is the aromatic amine derivative according to claim 1.

17. An organic electroluminescence device, comprising an organic thin film layer formed of one or more layers including a light emitting layer and interposed between a cathode and an anode, wherein a layer of the organic thin film layer contains the aromatic amine derivative according to claim 1 by itself or as a component of a mixture.

18. The organic electroluminescence device according to claim 17, wherein the light emitting layer contains the aromatic amine derivative.

19. The organic electroluminescence device according to claim 17, wherein the light emitting layer contains the aromatic amine derivative as a doping material and contains an anthracene derivative represented by the following general formula (i) as a host material:

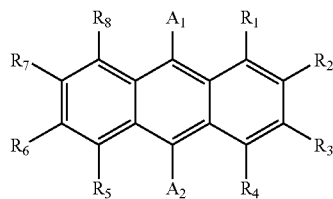

(i)

where $A_1$ and $A_2$ each independently represent a group derived from a substituted or unsubstituted aromatic ring having 6 to 20 ring-forming carbon atoms, $R_1$ to $R_8$ each independently represent a group selected from a hydrogen atom, a substituted or unsubstituted aryl group having 6 to 50 ring-forming carbon atoms, a substituted or unsubstituted heteroaryl group having 4 to 50 ring-forming atoms, a substituted or unsubstituted alkyl group having 1 to 50 carbon atoms, a substituted or unsubstituted cycloalkyl group having 3 to 50 ring-forming carbon atoms, a substituted or unsubstituted alkoxy group having 1 to 50 carbon atoms, a substituted or unsubstituted aralkyl group having 7 to 50 ring-forming carbon atoms, a substituted or unsubstituted aryloxy group having 6 to 50 ring-forming carbon atoms, a substituted or unsubstituted arylthio group having 6 to 50 ring-forming carbon atoms, a substituted or unsubstituted alkoxycarbonyl group having 1 to 50 carbon atoms, a substituted or unsubstituted silyl group, a carboxyl group, a halogen atom, a cyano group, a nitro group, and a hydroxyl group.

20. The organic electroluminescence device according to claim 19, wherein $A_1$ and $A_2$ in the general formula (i) represent groups different from each other.

21. The organic electroluminescence device according to claim 17, wherein the light emitting layer contains the aromatic amine derivative as a doping material and contains a pyrene derivative represented by the following general formula (ii) as a host material:

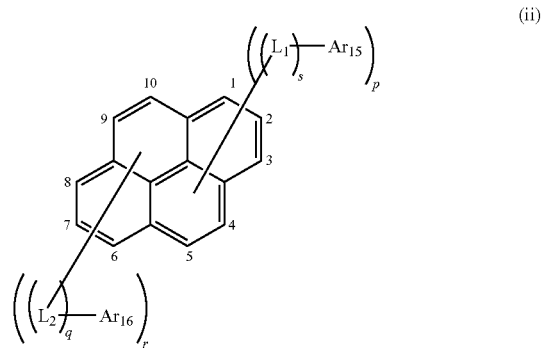

(ii)

where:
$Ar_{15}$ and $Ar_{16}$ each independently represent a substituted or unsubstituted aryl group having 6 to 50 ring-forming carbon atoms;

$L_1$ and $L_2$ each independently represent a substituted or unsubstituted phenylene group, a substituted or unsubstituted naphthalenylene group, a substituted or unsubstituted fluorenylene group, or a substituted or unsubstituted dibenzosilolylene group;

s represents an integer of 0 to 2, p represents an integer of 1 to 4, q represents an integer of 0 to 2, and r represents an integer of 0 to 4; and $L_1$ or $Ar_{15}$ is bonded to any one of 1- to 5-positions of pyrene and $L_2$ or $Ar_{16}$ is bonded to any one of 6- to 10-positions of pyrene, provided that, when p+r is an even number, $Ar_{15}$, $Ar_{16}$, $L_1$, and $L_2$ satisfy the following condition (1) or (2):

(1) $Ar_{15} \neq Ar_{16}$ and/or $L_1 \neq L_2$ where ≠ means that groups on both of its sides are different from each other in structure; or (2) when $Ar_{15} = Ar_{16}$ and $L_1 = L_2$, (2-1) s≠q and/or p≠r, or (2-2) if s=q and p=r, (2-2-1) $L_1$ and $L_2$ are, or pyrene is, bonded to different bonding positions on $Ar_{15}$ and $Ar_{16}$, or (2-2-2) in the case where $L_1$ and $L_2$ are, or pyrene is, bonded to the same bonding positions on $Ar_{15}$ and $Ar_{16}$, substitution positions of $L_1$ and $L_2$ or $Ar_{15}$ and $Ar_{16}$ on pyrene exclude 1- and 6-positions or 2- and 7-positions.

* * * * *